United States Patent
Davis et al.

(10) Patent No.: US 8,114,983 B2
(45) Date of Patent: Feb. 14, 2012

(54) COMPOSITIONS AND USE OF EPAS1 INHIBITORS

(75) Inventors: Mark E. Davis, Pasadena, CA (US); Jeremy D. Heidel, Madison, WI (US); Joanna Yi-Ching Liu, Arcadia, CA (US)

(73) Assignee: Calando Pharmaceuticals, Inc., Pasadena, CA (US)

( * ) Notice: Subject to any disclaimer, the term of this patent is extended or adjusted under 35 U.S.C. 154(b) by 301 days.

(21) Appl. No.: 12/384,475

(22) Filed: Apr. 3, 2009

(65) Prior Publication Data

US 2010/0010071 A1 Jan. 14, 2010

Related U.S. Application Data

(60) Provisional application No. 61/123,069, filed on Apr. 4, 2008.

(51) Int. Cl.
*C07H 21/04* (2006.01)
*A61K 31/70* (2006.01)
(52) U.S. Cl. .......................................... 536/24.5; 514/44
(58) Field of Classification Search ........................ None
See application file for complete search history.

(56) References Cited

U.S. PATENT DOCUMENTS

2004/0220393 A1 11/2004 Ward et al.
2007/0031844 A1* 2/2007 Khvorova et al. ................ 435/6

FOREIGN PATENT DOCUMENTS

WO WO 2004/076639 A2 9/2004
WO WO 2007/055547 A1 5/2007
WO WO 2009079452 A2 * 6/2009

OTHER PUBLICATIONS

Database EMBL [Online], "*Homo sapiens* piRNA piR-47460, complete sequence." XP002549880, retrieved from EPI accession No. EMBL:DQ579348, Database accession No. DQ579348, the whole document, 2006.
Sowter et al., "Predominant role of hypoxia-inducible transcription factor (Hif)-1alpha versus Hif-2alpha in regulation of the transcriptional response to hypoxis." Cancer Research, vol. 63(19), pp. 6130-6134 (2003).
Takeda et al., "Endothelial PAS domain protein 1 gene promotes angiogenesis through the transactivation of both vascular endothelial growth factor and its receptor, Flt-1." Circulation Research, vol. 95(2), pp. 146-153 (2004).

* cited by examiner

*Primary Examiner* — Tracy Vivlemore
(74) *Attorney, Agent, or Firm* — Fanelli Haag PLLC

(57) ABSTRACT

The present invention relates to inhibitors of endothelial PAS domain protein 1 (EPAS1), and methods and compositions related to the EPAS1 inhibitors. In certain embodiments, the EPAS1 inhibitors include nucleic acids, such as for example siRNAs.

39 Claims, 9 Drawing Sheets hEPAS1 mRNA [GenBank seq # NM 001430] (SEQ ID NO: 1)

ORIGIN
```
   1 gccacacggg tccggtgccc gctgcgcttc cgccccagcg ctcctgaggc ggccgtacaa
  61 tcctcggcag tgtcctgaga ctgtatggtc agctcagccc ggcctccgac tccttccgac
 121 tcccagcatt cgagccactt tttttttttct ttgaaaactc agaaaagtga ctccttttcc
 181 agggaaaaag gaacttgggt tcccttctct ccgtcctctt ttcgggtctg acagcctcca
 241 cccactcctt ccccggaccc cgcctccgcg cgcaggttcc tcccagtcac ctttctccac
 301 ccccgccccc gcacctagcc cgccgcgcgc caccttccac ctgactgcgc ggggcgctcg
 361 ggacctgcgc gcacctcgga ccttcaccac ccgccgggc cgcggggagc ggacgagggc
 421 cacagccccc cacccgccag ggagcccagg tgctcggcgt ctgaacgtct caaagggcca
 481 cagcgacaat gacagctgac aaggagaaga aaggagtag ctcggagagg aggaaggaga
 541 agtcccggga tgctgcgcgg tgccggcgga gcaaggagac ggaggtgttc tatgagctgg
 601 cccatgagct gcctctgccc cacagtgtga gctcccatct ggacaaggcc tccatcatgc
 661 gactggcaat cagcttcctg cgaacacaca agctcctctc ctcagtttgc tctgaaaacg
 721 agtccgaagc cgaagctgac cagcagatgg acaacttgta cctgaaagcc ttggagggtt
 781 tcattgccgt ggtgacccaa gatggcgaca tgatctttct gtcagaaaac atcagcaagt
 841 tcatgggact tacacaggtg gagctaacag gacatagtat ctttgactc actcatccct
 901 gcgaccatga ggagattcgt gagaacctga gtctcaaaaa tggctctggt tttgggaaaa
 961 aaagcaaaga catgtccaca gagcgggact tcttcatgag gatgaagtgc acggtcacca
1021 acagaggccg tactgtcaac ctcaagtcag ccacctggaa ggtcttgcac tgcacgggcc
1081 aggtgaaagt ctacaacaac tgccctcctc acaatagtct gtgtggctac aaggagcccc
1141 tgctgtcctg cctcatcatc atgtgtgaac caatccagca cccatcccac atggacatcc
1201 ccctggatag caagaccttc ctgagccgcc acagcatgga catgaagttc acctactgtg
1261 atgacagaat cacagaactg attggttacc accctgagga gctgcttggc cgctcagcct
1321 atgaattcta ccatgcgcta gactccgaga acatgaccaa gagtcaccag aacttgtgca
1381 ccaagggtca ggtagtaagt ggccagtacc ggatgctcgc aaagcatggg ggctacgtgt
1441 ggctggagac ccaggggacg gtcatctaca accctcgcaa cctgcagccc cagtgcatca
1501 tgtgtgtcaa ctacgtcctg agtgagattg agaagaatga cgtggtgttc tccatggacc
1561 agactgaatc cctgttcaag ccccacctga tggccatgaa cagcatcttt gatagcagtg
1621 gcaaggggc tgtgtctgag aagagtaact tcctattcac caagctaaag gaggagcccg
1681 aggagctggc ccagctggct cccacccag gagacgccat catctctctg gatttcggga
1741 atcagaactt cgaggagtcc tcagcctatg caaggccat cctgccccg agccagccat
1801 gggccacgga gttgaggagc cacagcaccc agagcgaggc tgggagcctg cctgccttca
1861 ccgtgcccca ggcagctgcc ccgggcagca ccaccccag tgccaccagc agcagcagca
1921 gctgctccac gcccaatagc cctgaagact attacacatc tttggataac gacctgaaga
1981 ttgaagtgat tgagaagctc ttcgccatgg acacagaggc caaggaccaa tgcagtaccc
2041 agacggattt caatgagctg gacttggaga cactggcacc ctatatcccc atggacgggg
2101 aagacttcca gctaagcccc atctgccccg aggagcggct cttggcggag aaccacagt
2161 ccaccccca gcactgcttc agtgccatga caaacatctt ccagccactg gcccctgtag
2221 ccccgcacag tccttcctc ctggacaagt tcagcagca gctggagagc aagaagacag
2281 agcccgagca ccggccatg tcctccatct tctttgatgc cggaagcaaa gcatccctgc
2341 caccgtgctg tggccaggcc agcacccctc tctcttccat gggggggcaga tccaataccc
2401 agtggccccc agatccacca ttacattttg ggcccacaaa gtgggccgtc ggggatcagc
2461 gcacagagtt cttgggagca cgccgttgg ggcccctgt ctctccaccc catgtctcca
2521 ccttcaagac aaggtctgca aagggttttg gggctcgagg cccagacgtg ctgagtccgg
```

Figure 1

SEQ ID NO: 1 (con't)

```
2581 ccatggtagc cctctccaac aagctgaagc tgaagcgaca gctggagtat gaagagcaag
2641 ccttccagga cctgagcggg ggggacccac ctggtggcag cacctcacat ttgatgtgga
2701 aacggatgaa gaacctcagg ggtgggagct gccctttgat gccggacaag ccactgagcg
2761 caaatgtacc caatgataag ttcacccaaa accccatgag gggcctgggc catcccctga
2821 gacatctgcc gctgccacag cctccatctg ccatcagtcc cggggagaac agcaagagca
2881 ggttcccccc acagtgctac gccacccagt accaggacta cagcctgtcg tcagcccaca
2941 aggtgtcagg catggcaagc cggctgctcg ggccctcatt tgagtcctac ctgctgcccg
3001 aactgaccag atatgactgt gaggtgaacg tgcccgtgct gggaagctcc acgctcctgc
3061 aaggagggga cctcctcaga gccctggacc aggccacctg agccaggcct tctacctggg
3121 cagcacctct gccgacgccg tcccaccagc ttcactctct ccgtctgttt ttgcaactag
3181 gtatttctaa cgccagcaca ctatttacaa gatggactta cctggcagac ttgcccaggt
3241 caccaagcag tggccttttt ctgagatgct cactttatta tccctatttt taaagtacac
3301 aattgtttta cctgttctga aatgttctta aattttgtag gatttttttc ctcccacct
3361 tcaatgactt ctaatttata ttatccatag gtttctctcc ctccttctcc ttctcacaca
3421 caactgtcca tactaacaag tttggtgcat gtctgttctt ctgtagggag aagctttagc
3481 ttcattttac taaaaagatt cctcgttatt gttgttgcca aagagaaaca aaaatgattt
3541 tgctttccaa gcttggtttg tggcgtctcc ctcgcagagc ccttctcgtt tcttttttaa
3601 actaatcacc atattgtaaa tttcagggtt tttttttttt tgtttaagct gactctttgc
3661 tctaattttg gaaaaaaaga aatgtgaagg gtcaactcca acgtatgtgg ttatctgtga
3721 aagttgcaca gcgtggcttt tcctaaactg gtgttttttcc cccgcatttg gtggattttt
3781 tattattatt caaaaacata actgagtttt taaaagagg agaaaattta tatctgggtt
3841 aagtgtttat catatatatg ggtactttgt aatatctaaa aacttagaaa cggaaatgga
3901 atcctgctca caaaatcact ttaagatctt ttcgaagctg ttaattttc ttagtgttgt
3961 ggacactgca gacttgtcca gtgctcccac ggcctgtacg gacactgtgg aaggcctccc
4021 tctgtcggct ttttgccatc tgtgatatgc cataggtgtg acaatccgag cagtggagtc
4081 attcagcggg agcactgcgc gctatcccct cacattctct atgtactatg tatgtatgta
4141 ttattattat tgctgccaag agggtctgat ggcacgttgt ggggtcgggg ggtggggcgg
4201 ggaagtgctc taactttct taaggttttg ttgctagccc ttcaagtgca ctgagctatg
4261 tgactcggat ggtcttcac acggcacatt tggacatttc cagaactacc atgagatggt
4321 ttagacggga attcatgcaa atgagggggtc aaaaatggta tagtgacccc gtccacgtcc
4381 tccaagctca cgaccttgga gccccgtgga gctggactga ggaggaggct gcacagcggg
4441 agagcagctg gtccagacca gcccgtgcagc ccccactcag ccggcagcca gatggccccg
4501 caaggcctcc agggatggcc cctagccaca ggccctggct gaggtctctg ggtcggtcag
4561 tgacatgtag gtaggaagca ctgaaaatag tgttcccaga gcactttgca actccctggg
4621 taagagggac gacacctctg gtttttcaat accaattaca tggaactttt ctgtaatggg
4681 tacaatgaag aagtttctaa aaacacacac aaagcacatt gggccaacta tttagtaagc
4741 ccggatagac ttattgccaa aaacaaaaaa tagctttcaa aagaaattta agttctatga
4801 gaaattcctt agtcatggtg ttgcgtaaat catattttag ctgcacggca ttaccccaca
4861 cagggtggca gaacttgaag ggttactgac gtgtaaatgc tggtatttga tttcctgtgt
4921 gtgttgccct ggcattaagg gcattttacc cttgcagttt tactaaaaca ctgaaaaata
4981 ttccaagctt catattaacc ctacctgtca acgtaacgat ttcatgaacg ttattatatt
5041 gtcgaattcc tactgacaac attataactg tatgggagct taactttata aggaaatgta
5101 tttttgacact ggtatcttat taaagtattc tgatcctaaa aaaaaaaaaa aaaaaaaaaa
5161 aaaaaaaaaa aaaaaaaaaa aaaaaa
```

Figure 1 (continued)

COMPOSITIONS AND USE OF EPAS1 INHIBITORS

RELATED APPLICATIONS

This application claims the benefit of priority to U.S. provisional application No. 61/123,069, filed Apr. 4, 2008. The specification of the foregoing application is hereby incorporated by reference in its entirety.

BACKGROUND

The transcriptional complex, hypoxia inducible factor (HIF), is a key regulator of oxygen homeostasis. Hypoxia induces the expression of genes participating in many cellular and physiological processes, including oxygen transport and iron metabolism, erythropoiesis, angiogenesis, glycolysis and glucose uptake, transcription, metabolism, pH regulation, growth-factor signaling, response to stress and cell adhesion. These gene products participate in either increasing oxygen delivery to hypoxic tissues or activating an alternative metabolic pathway (glycolysis) which does not require oxygen. Hypoxia-induced pathways, in addition to being required for normal cellular processes, can also aid tumor growth by allowing or aiding angiogenesis, immortalization, genetic instability, tissue invasion and metastasis (Harris, *Nat. Rev. Cancer* 2: 38-47, 2002; Maxwell et al., *Curr. Opin. Genet. Dev.* 11: 293-299, 2001).

HIF is a heterodimer composed of an alpha subunit complexed with a beta subunit, both of which are basic helix-loop-helix transcription factors. The beta subunit of HIF is a constitutive nuclear protein. The alpha subunit is the regulatory subunit specific to the oxygen response pathway, and can be one of three subunits, HIF1alpha, 2 alpha or 3 alpha (HIF1, HIF2α and HIF3α, respectively) (Maxwell et al., *Curr. Opin. Genet. Dev.* 11: 293-299, 2001; Safran and Kaelin, *J. Clin. Invest.* 111: 779-783, 2003).

Until a tumor establishes a blood supply, hypoxic conditions limit tumor growth. Subsequent increases in HIF1α activity result in increased expression of target genes such as vascular endothelial growth factor (VEGF). VEGF expression is essential for vascularization and the establishment of angiogenesis in most solid tumors (Iyer et al., *Genes Dev.* 12: 149-162, 1998). A significant association between HIF1α, VEGF overexpression and tumor grade is also seen in human glioblastoma multiforme, the highest grade glioma, in which mean patient survival time is less than one year. The rapidly proliferating tumor outgrows its blood supply, resulting in extensive necrosis, and these regions express high levels of HIF1α protein and VEGF mRNA, suggesting a response of the tumor to hypoxia (Zagzag et al., *Cancer* 88: 2606-2618, 2000).

The gene encoding HIF2α (also, endothelial PAS domain protein 1, EPAS1, MOP2, hypoxia-inducible factor 2, HIF-related factor, HRF, HIF1 alpha-like factor, HLF) was initially identified as a transcription factor expressed in endothelial cells (Ema et al., *Proc. Natl. Acad. Sci. U.S.A.* 94: 4273-4278, 1997; Flamme et al., *Mech. Dev.* 63: 51-60, 1997; Hogenesch et al., *J. Biol. Chem.* 272: 8581-8593, 1997; Tian et al., *Genes Dev.* 11: 72-82, 1997). A link between elevated EPAS1 activity and angiogenesis has been demonstrated by experiments that show how HIF activity regulates VEGF expression. Normal human kidney cells typically have low levels of EPAS1, but upon introduction of a vector encoding EPAS1 into these cells, VEGF mRNA and protein levels increase significantly (Xia et al., *Cancer* 91: 1429-1436, 2001). When EPAS1 was inhibited, VEGF expression was significantly decreased, thus demonstrating a direct link between EPAS1 activity and VEGF expression (Xia et al., *Cancer* 91: 1429-1436, 2001). A correlation between HIF activity and VEGF expression is also observed in malignant cells and tissues. EPAS1 can be readily detected in renal cell carcinoma (RCC) cell lines in the absence of a vector encoding EPAS1 (Xia et al., *Cancer* 91: 1429-1436, 2001). Significant increases in EPAS1 and VEGF mRNA in renal cell carcinoma tissue samples, compared to normal tissue, suggest that abnormal activation of EPAS1 may be involved in the angiogenesis of RCC (Xia et al., *Cancer* 91: 1429-1436, 2001).

In addition to RCC, the expression of EPAS1 in other malignancies has also been reported. EPAS1 is expressed at the levels of mRNA and protein in human bladder cancers, especially in those with an invasive phenotype (Xia et al., *Urology* 59: 774-778, 2002). Another example of overexpression of EPAS1 is seen in squamous cell head-and-neck cancer (SCHNC). Higher levels of EPAS1 were associated with locally aggressive behavior of SCHNC, as well as intensification of angiogenesis (Koukourakis et al., *Int. J. Radiat. Oncol. Biol. Phys.* 53: 1192-1202, 2002). These findings also demonstrated a link between overexpression of EPAS1 and resistance to chemotherapy. Yet another correlation between overexpression of EPAS1 and cancer is seen in malignant pheochromocytomas, which exhibit a higher level of EPAS1 and an induced VEGF pathway, when compared to benign counterparts (Favier et al., *Am. J. Pathol.* 161: 1235-1246, 2002). EPAS1 overexpression is also a common event in non-small-cell lung cancer (NSCLC) and is related to the up-regulation of multiple angiogenic factors and overexpression of angiogenic receptors by cancer cells. EPAS1 overexpression in NSCLC is an indicator of poor prognosis (Giatromanolaki et al., *Br. J. Cancer* 85: 881-890, 2001). Elevated levels of EPAS1 mRNA and protein are seen in human lung adenocarcinoma cells, and exposure of these cells to hypoxia further increases EPAS1 expression (Sato et al., *Am. J. Respir. Cell Mol. Biol.* 26: 127-134, 2002). Taken together, these studies demonstrate that elevated EPAS1 confers aggressive tumor behavior, and that targeting the HIF pathway may aid the treatment of several different types of cancers.

Furthermore, the hypoxia response element plays a role in constitutively upregulating an isoform of VEGF in cancer cell lines under nonnoxic conditions. The HRE located within a cell type-specific enhancer element in glioblastoma cells participates in the up-regulation of VEGF expression through enhanced binding of EPAS1 to the HRE (Liang et al., *J. Biol. Chem.* 277: 20087-20094, 2002). A truncated version of EPAS1 that can bind to hypoxia-inducible factor 1 beta, but not to the HRE, was unable to transactivate the VEGF promoter (Liang et al., *J. Biol. Chem.* 277: 20087-20094, 2002). This further demonstrates the capability of cancer cells to combat hypoxic conditions by enhancing expression of factors required for vascularization and angiogenesis.

As a consequence of EPAS1 involvement in many diseases, there remains a long felt need for additional agents capable of effectively regulating EPAS1 function. Such inhibition is especially important in the treatment of cancer, given that the upregulation of expression of EPAS1 is associated with many different types of cancer.

BRIEF DESCRIPTION OF THE INVENTION

The present disclosure provides compositions and methods for modulating EPAS1 expression. In particular, RNAi compositions for modulating EPAS1 expression are believed to be useful to treat abnormal proliferative conditions associated with EPAS1. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels. Inhibition of EPAS1 may be a particularly useful approach for the treatment of such disorders.

Accordingly, the present invention provides EPAS1 inhibitors, and their related methods and compositions that can achieve inhibition of EPAS1 in target cells. In particular, target cells include those cells undergoing unwanted proliferation such as cancer or tumor cells, cells undergoing excessive growth and/or proliferation associated with certain diseases or conditions (e.g., T cells in autoimmune diseases or rejection of transplants), and pathogens (e.g., bacteria and fungal cells). The EPAS1 inhibitors of the invention may inhibit EPAS1 by decreasing EPAS1 expression or a biological function of EPAS1 (e.g., an enzymatic activity of EPAS1).

An EPAS1 inhibitor can be a nucleic acid, a small molecule, a peptide including an antibody, a peptide derivative, or a peptidomimetic.

Certain embodiments relate to EPAS1 inhibitors that are nucleic acids. The invention provides isolated nucleic acids comprising at least a portion that hybridizes to an EPAS1 transcript under certain conditions (e.g., physiological or intracellular) and decreases the expression of target gene in a cell. The target gene transcript may be any pre-splicing transcript (i.e., including introns), post-splicing transcript, as well as any splice variant. In certain embodiments, the target gene transcript has a sequence set forth in SEQ ID NO: 1. Examples of categories of nucleic acids include, for example, RNAi constructs and catalytic nucleic acid constructs. A nucleic acid may be single- or double-stranded. A double-stranded nucleic acid may also include regions of overhang or non-complementarity, where one or the other of the strands is single-stranded. A single-stranded nucleic acid may include regions of self-complementarity, meaning that the compound forms a so-called "hairpin" or "stem-loop" structure, with a region of double helical structure. A nucleic acid may comprise a nucleotide sequence that is complementary to a region consisting of no more than 1000, no more than 500, no more than 250, no more than 100 or no more than 50 nucleotides of the target gene nucleic acid sequence such as that designated by SEQ ID NO: 1 (FIG. 1), or any homologs (e.g., orthologs and paralogs) or variants thereof (e.g., allelic variants). The region of complementarity will preferably be at least 8 nucleotides, and optionally at least 10, 15, 20, 21, 22, 23, 24, 25, 26, 27, 28, 29, or 30 nucleotides. A region of complementarity may fall within an intron, a coding sequence or a noncoding sequence of the target gene transcript. Generally, a nucleic acid will have a length of about 8 to about 500 nucleotides or base pairs in length, and optionally the length will be about 14 to about 50 nucleotides. A nucleic acid may be a DNA, RNA or RNA:DNA hybrid. Any one strand may include a mixture of DNA and RNA, as well as modified forms that cannot readily be classified as either DNA or RNA. Likewise, a double-stranded nucleic acid may be DNA:DNA, DNA:RNA, or RNA:RNA, and any one strand may also include a mixture of DNA and RNA, as well as modified forms that cannot readily be classified as either DNA or RNA. A nucleic acid may include any of a variety of modifications, including one or more modifications to the backbone (the sugar-phosphate portion in a natural nucleic acid, including internucleotide linkages) or the base portion (the purine or pyrimidine portion of a natural nucleic acid). A nucleic acid will preferably have a length of about 15 to about 30 nucleotides and will often contain one or more modifications to improve characteristics such as stability in the serum, in a cell or in a place where the nucleic acid is likely to be delivered, such as the stomach in the case of orally delivered nucleic acids and the lung for inhaled nucleic acids. In the case of an RNAi construct, the strand complementary to the target transcript will generally be RNA or modifications thereof. The other strand may be RNA, DNA or any other variation. The duplex portion of a double-stranded or single-stranded "hairpin" RNAi construct will preferably have a length of 18 to 30 nucleotides in length and optionally about 21 to 27 nucleotides in length. Catalytic or enzymatic nucleic acids may be ribozymes or DNA enzymes and may also contain modified forms. Nucleic acids herein may inhibit expression of the target EPAS1 gene by about 50%, 75%, 90% or more when contacted with cells under physiological conditions and at a concentration where a nonsense or sense control has little or no effect. Preferred concentrations for testing the effect of nucleic acids are 1, 5, 10, 20, 50, 100, or 1000 nanomolar. Nucleic acids herein may also be tested for effects on cellular phenotypes. In the case of certain cancer cell lines, cell death or decreased rate of expansion may be measured upon administration of the targeted nucleic acids. Preferably, cell expansion will be inhibited by greater than 50% at an experimentally-meaningful concentration of the nucleic acid.

In certain aspects, the invention provides pharmaceutical compositions comprising any of the various EPAS1 inhibitors, e.g., nucleic acids targeting an EPAS1 gene (or targeted nucleic acids). A pharmaceutical composition will generally include a pharmaceutically-acceptable carrier. A pharmaceutical composition may comprise a nucleic acid that hybridizes to the target gene transcript under physiological conditions and decreases the expression of the target gene in a cell.

In certain aspects, the invention provides methods for inhibiting expression of an EPAS1 gene in a cell. The method may comprise contacting the cell with an effective amount of a nucleic acid that hybridizes to the target EPAS1 transcript under physiological conditions and decreases the expression of target gene in a cell. Any of the nucleic acids targeting EPAS1 disclosed may be used in such a method. The cell may be a tumor or cancerous cell, a pathogen cell, or a normal cell. In certain embodiments, the normal cell undergoes unwanted proliferation that leads to a certain disease or condition in a patient.

In certain aspects, the invention provides methods for reducing the growth rate of a tumor in a subject, comprising administering an amount of an EPAS1 inhibitor herein sufficient to reduce the growth rate of the tumor. In certain aspects, the invention provides methods for treating a patient suffering from a cancer, comprising administering to the patient an EPAS1 inhibitor herein. The EPAS1 inhibitor may be a nucleic acid, for example, an RNAi nucleic acid or a catalytic nucleic acid, and may be formulated with a pharmaceutically-acceptable carrier. Optionally, the tumor will comprise one or more cancer cells expressing the gene that the nucleic acid targets. The target EPAS1 gene may be overexpressed relative to a non-cancerous cell from a comparable tissue. The tumor may also be a metastatic tumor. Such treatment may be combined with at least one additional anti-cancer chemotherapeutic agent that inhibits cancer cells in an additive or synergistic manner with the nucleic acid. The nucleic acid and the additional anticancer agent(s) may be formulated together as a combination formulation, or may be formulated independently and administered in such a manner (e.g., timing, dosage) so as to achieve the combined effect.

In certain aspects, the invention provides for the use of a nucleic acid in the manufacture of a medicament for the treatment of, for example, cancer or infection by a pathogen.

In certain aspects, the invention provides methods and compositions for removing or reducing a pathogen from a patient infected or an object contaminated by the pathogen.

Another aspect of the present invention provides a packaged pharmaceutical. Such packaged pharmaceutical comprises: (i) a therapeutically-effective amount of an inhibitor disclosed herein that targets an EPAS1 gene; and (ii) instructions and/or a label for administration of the EPAS1 inhibitor for the treatment of patients having tumors that express the EPAS1 gene.

Another aspect of the present invention provides a packaged disinfectant. The packaged disinfectant can be specific against one or more infectious agents such as pathogens. Such packaged disinfectant comprises: (i) an effective amount of an EPAS1 inhibitor that targets an EPAS1 gene in the infectious agent; and (ii) instructions and/or label for administration of the EPAS1 inhibitor for removing or reducing the quantity of the infectious agent.

BRIEF DESCRIPTION OF THE DRAWINGS

FIG. 1 shows the cDNA sequence for human EPAS1 (GenBank Accession No. NM_001430) (SEQ ID NO: 1). The three 11-base stretches underlined and in bold correspond to the core target sequences as represented by SEQ ID NOs: 2-4.

SUMMARY OF THE INVENTION

Figure 2:
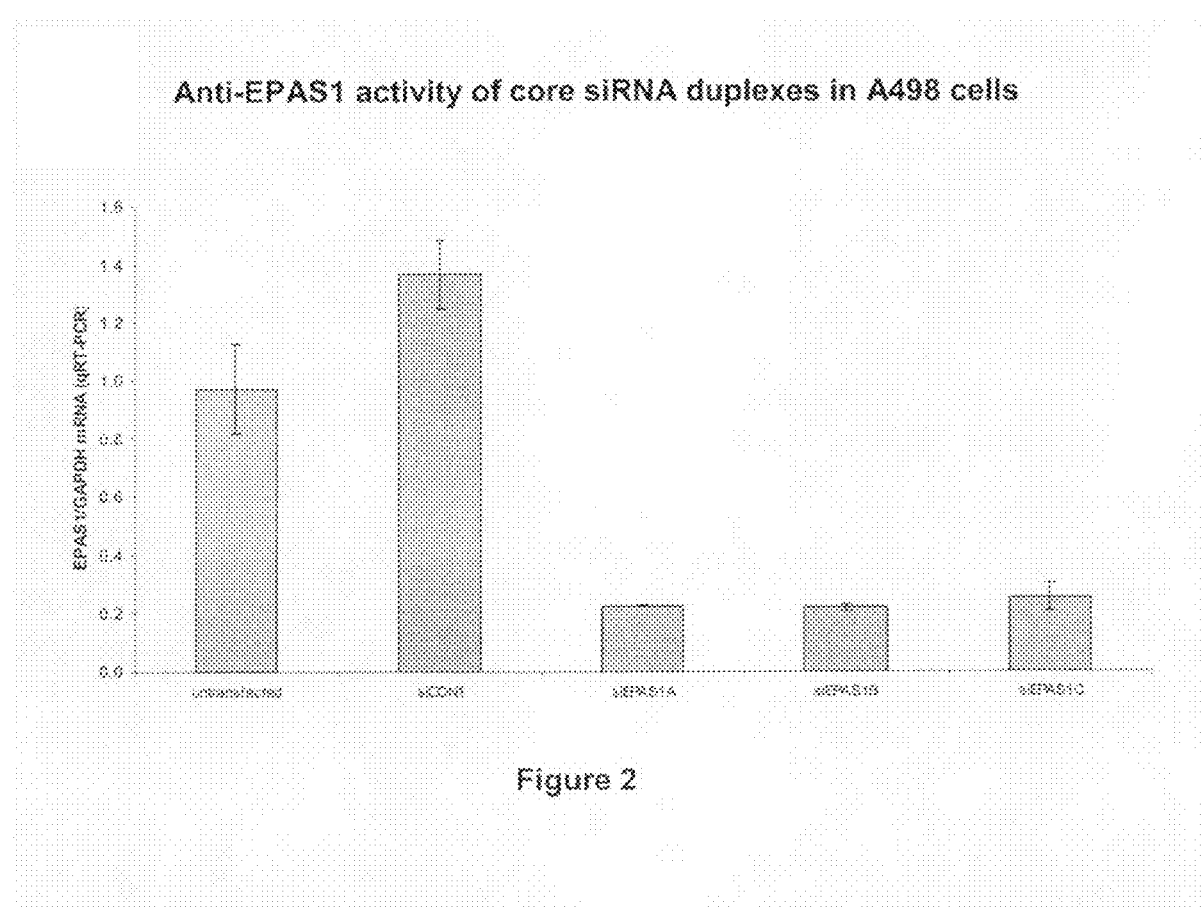
FIG. 2 depicts the evaluation of anti-EPAS1 activity of initial three siRNA duplexes—siEPAS1A (SEQ ID NOs: 5 and 6), siEPAS1B (SEQ ID NOs: 7 and 8), and siEPAS1C (SEQ ID NOs: 9 and 10)—in A498 (human kidney carcinoma) cells. While siCON1 did not show any EPAS1 down-regulation (relative to untransfected cells), all three siRNAs against EPAS1 exhibited significant down-regulation of EPAS1 mRNA.

One aspect of the invention relates to a nucleic acid comprising a first strand of about 15 to about 30 nucleotides in length that comprises a sequence selected from SEQ ID NOs: 2-4, and a second strand of about 15 to about 30 nucleotides in length, wherein at least 12 nucleotides of the first and second strands are complementary to each other and form a double-stranded nucleic acid under physiological conditions, and wherein the double-stranded nucleic acid can reduce the expression of endothelial PAS domain protein 1 (EPAS1) in a cell by an RNA interference mechanism.

In certain embodiments, the nucleic acid is a double-stranded RNA, wherein the double-stranded portion is optionally about 15 to about 30 nucleotides in length. In other embodiments, the nucleic acid is a hairpin RNA comprising a loop region optionally having about 4 to about 10 nucleotides in length. In another embodiment, the first strand is a DNA polynucleotide and the second strand is an RNA polynucleotide. In some embodiments, the first and/or second strand may further comprise a 3' overhang region, a 5' overhang region, or both 3' and 5' overhang regions, wherein the overhang region optionally contains about 1 to about 10 nucleotides in length.

Additionally, in any of the embodiments disclosed herein, the nucleic acid may comprise one or more modified backbone or base moieties. Such modifications may be, for example, one or more of the following: alkylphosphonates, phosphorothioates, phosphorodithioates, alkylphosphonothioates, phosphoramidates, phosphate esters, carbamates, acetamidate, carboxylmethyl esters, carbonates, and phosphate triesters. The modified backbone or base moieties optionally comprise at least one 2'-O-alkylated ribonucleotide.

In any of the disclosed embodiments, the first strand may comprise a sequence selected from SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, and 81. Similarly, the second strand may comprise a sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, and 82.

In certain embodiments, a nucleic acid described above, and/or a nucleic acid of any of the above applicable combinations, inhibits EPAS1 expression in cells by 50% or greater, when contacted with the cells under physiological conditions, e.g., at a concentration of about 10 or about 20 nanomolar.

In another aspect, the invention relates to an isolated nucleic acid comprising a sequence that hybridizes to a region of an EPAS1 transcript corresponding to nucleotides 655-718, 2878-2929, or 4978-5039 of SEQ ID NO: 1 under physiological conditions and decreases the expression of EPAS1 in a cell. In certain embodiments, the nucleic acid comprises a sequence that hybridizes to a region of an EPAS1 transcript corresponding to nucleotides 665-708, 2888-2919, or 4988-5029 of SEQ ID NO: 1. In particular embodiments, the nucleic acid comprises a sequence that hybridizes to a region of an EPAS1 transcript corresponding to nucleotides 670-703, 2893-2914, or 4992-5024 of SEQ ID NO: 1.

The nucleic acid may comprise at least 10 consecutive nucleotides that are complementary to one of said regions of EPAS1. In some embodiments, the nucleic acid is from about 14 to about 50 nucleotides in length. The nucleic acid may be single-stranded, or double-stranded. In certain embodiments, the nucleic acid is a DNA molecule, optionally comprising one or more modified backbone or base moieties, e.g., as disclosed above. Further, the nucleic acid may be an RNA molecule, optionally comprising one or more modified backbone or base moieties. In certain embodiments, the nucleic acid may comprise a DNA strand and an RNA strand and optionally comprises one or more modified backbone or base moieties.

In certain embodiments, the nucleic acid is an RNAi construct, wherein the RNAi construct is optionally a dsRNA, comprising, for example, one or more modified backbone or base moieties. The RNAi construct is optionally a hairpin RNA, comprising, for example, one or more modified backbone or base moieties. The duplex portion of the RNAi construct may be from about 15 to about 30 nucleotides in length. In certain embodiments, the RNAi construct comprises a sequence selected from SEQ ID NOs: 2-4, optionally comprising one or more modified backbone or base moieties. In certain embodiments, the RNAi construct comprises a sequence selected from SEQ ID NOs: 5-82, optionally comprising one or more modified backbone or base moieties. Further, the RNAi construct optionally comprises one or more modified backbone or base moieties, optionally comprising at least one internucleotide linkage selected from, for example, alkylphosphonates, phosphorothioates, phosphorodithioates, alkylphosphonothioates, phosphoramidates, phosphate esters, carbamates, acetamidate, carboxylmethyl esters, carbonates, and phosphate triesters. Additionally, the RNAi also optionally comprises at least one 2'-O-alkylated ribonucleotide.

In other embodiments, the nucleic acid is an enzymatic nucleic acid, e.g., a ribozyme or a DNA enzyme.

A nucleic acid as described above, and/or a nucleic acid of any of the above applicable combinations, may inhibit EPAS1 expression in cells by 50% or greater, when contacted with the cells under physiological conditions, e.g., at a concentration of about 10 or about 20 nanomolar.

Another aspect of the invention relates to a pharmaceutical composition comprising a nucleic acid as described above and a pharmaceutically acceptable carrier.

In one embodiment, the pharmaceutically acceptable carrier includes a cationic polymer. The pharmaceutically acceptable carrier may also include a cyclodextrin polymer, e.g., im-CDP. Further, the pharmaceutical composition may comprise a particle that includes a cyclodextrin polymer and the nucleic acid as described above, and/or be PEGylated. The particle further optionally comprises adamantane. In another embodiment, the pharmaceutical composition further comprises a ligand that targets a particular tissue or cell type, wherein the ligand optionally comprises transferrin.

In certain embodiments, the pharmaceutical composition comprises nanoparticles, wherein the nanoparticles are from about 10 to about 100 nm in diameter such as from about 50 to about 70 nm in diameter, e.g., about 50 nm in diameter.

In certain embodiments, the pharmaceutically acceptable carrier comprises: an imidazole-modified cyclodextrin-containing cationic polymer, and a targeting moiety comprising adamantane-PEG-ligand, wherein the polymer and targeting moiety form nanoparticles that encapsulate the nucleic acid. The nanoparticles optionally have a diameter of about 50 to about 120 nm, such as from about 50 to about 100 nm, e.g., from about 50 to about 70 nm, or even about 50 nm. The targeting ligand may optionally comprise galactose and/or transferrin.

In further aspects, the invention relates to the use of the nucleic acid according to any one of the nucleic acids described above in the manufacture of a medicament for the treatment of a disease or condition associated with unwanted proliferation of cells. In certain embodiments, the cells are cancerous or tumor cells. In other embodiments, the cells are pathogen cells. In some embodiments, the cells may be normal cells, the unwanted proliferation of which leads to the disease or condition.

In other aspects, the invention relates to a method for treating a patient having a cancer comprising administering to the patient a therapeutically effective amount of the double-stranded nucleic acid as described above.

In certain embodiments, the method further comprises administering at least one additional anti-cancer chemotherapeutic agent, e.g., fluorouracil (5FU), that inhibits proliferation of cancer cells, e.g., in an additive or synergistic manner with the nucleic acid. In certain embodiments, the cancer cell expresses a higher level of EPAS1 compared to a noncancerous cell from a comparable tissue. In certain embodiments, the nucleic acid may be formulated with a pharmaceutically acceptable carrier. In certain embodiments, the nucleic acid is formulated with a ligand targeting the cancer cell, such as a clear-cell renal cell carcinoma, e.g., wherein the ligand comprises transferrin and/or galactose.

The nucleic acid may be formulated as a component of a polymeric nanoparticle, wherein the nanoparticle is optionally from about 10 to about 120 nm in diameter, such as from about 50 to about 120 nm in diameter, e.g., from about 50 to about 100 nm in diameter, or even about 50 nm in diameter.

Another aspect of the invention relates to a method of treating a patient having a cancer comprising administering to the patient a therapeutically effective amount of a double-stranded nucleic acid to reduce expression of EPAS1 by an RNAi mechanism and one or more anti-cancer agents that induce EPAS1 expression.

In certain embodiments, the nucleic acid is formulated with a pharmaceutically acceptable carrier. In certain embodiments, the nucleic acid is formulated with a ligand targeting the cancer cell, such as a clear-cell renal cell carcinoma, e.g., wherein the ligand optionally comprises tranferrin and/or galactose.

The nucleic acid may be formulated as a component of a polymeric nanoparticle, wherein the nanoparticle is optionally from about 10 to about 120 nm in diameter, such as from about 50 to about 120 nm in diameter, e.g., from about 50 to about 100 nm in diameter, or even about 50 nm in diameter.

In certain embodiments described above or elsewhere, a therapeutically effective amount of the nucleic acid may be administered systemically.

A method described above may further comprise determining the level of von Hippel-Lindau (VHL) protein activity in the patient prior to administering the nucleic acid, wherein said activity is optionally determined by measuring a decrease in RNA or protein level of VHL in the patient as compared to said levels in a healthy subject. In other embodiments, said activity may be determined by a genetic screening to identify one or more mutations in the VHL gene, said one or more mutations comprising one or more of the following: a truncation-causing mutation, a mutation that causes allelic loss, a nonsense mutation, a frameshift mutation, a promoter mutation, an enhancer mutation, splice site mutation, null mutation, and poly-A tail mutation.

DETAILED DESCRIPTION OF THE INVENTION

Overview

EPAS1 activation results in the upregulation of HIF target genes, notably those encoding VEGF, TGF-alpha, Met, stromal cell-derived factor (SDF)-1, and chemokine receptor CXCR4, among others (Soccio et al., *Jour. Biol. Chem.* 280: 19410-19418, 2005; Kim and Kaelin, *J. Clin. Onocology* 22:4991-5004, 2004). As such, it is a desirable cancer therapeutic target. In particular, EPAS1 upregulation has been closely associated with renal cell carcinoma, and is due, in part, to its association with the von Hippel-Lindau tumor suppressor gene (VHL). Inactivation of VHL is linked to the development of various VHL-associated abnormalities, particularly clear-cell renal cell carcinoma (RCC). The VHL gene product, pVHL, is part of a complex that recognizes the α subunit of HIF and targets it for polyubiquitination and proteasomal degradation. Therefore, VHL-deficient cancer cells have increased levels of HIF, making them good candidates for treatment that reduces cellular HIF levels.

Inhibition of EPAS1 may be achieved by inhibiting a biological activity of EPAS1 in a cell, such as its enzymatic activity. Alternatively, inhibition of EPAS1 may be achieved by inhibiting expression of an EPAS1 gene in a cell. Small molecules and nucleic acids are available to down-regulate EPAS1 activity and/or expression. Some examples include antisense molecules (e.g., U.S. Pat. No. 7,217,572) and short hairpin RNAs as described in Kondo et al. 1(3): 439-444, 2003 and Zimmer et al. 2:89-95, 2004). Nevertheless, novel and improved EPAS1 inhibitors remain desirable as new tools to down-regulate EPAS1.

Nucleic Acid EPAS1 Inhibitors

In certain aspects, the subject invention provides nucleic acid inhibitors of an EPAS1 gene and methods for inhibiting or reducing the activity of an EPAS1 gene or protein, for example, by reducing or down-regulating expression of an EPAS1 gene. By "inhibit" or "reduce," it is meant that the expression of the gene, or level of nucleic acids or equivalent nucleic acids encoding one or more proteins or protein subunits, is reduced below that observed in the absence of the nucleic acid agents of the subject invention.

As used herein, the term "nucleic acid" or "nucleic acid agent" refers to any nucleic acid-based compound that contains nucleotides and has a desired effect on an EPAS1 gene. The nucleic acids can be single-, double-, or multiple-stranded, and can comprise modified or unmodified nucleotides or non-nucleotides or various mixtures, and combinations thereof. Examples of nucleic acid agents of the subject invention include, but are not limited to, dsRNA, siRNA, and enzymatic nucleic acids.

In certain embodiments, the subject invention provides nucleic acid inhibitors that are targeted to an EPAS1 gene or mRNA from one or more species, including eukaryotes or prokaryotes. In certain embodiments, the nucleic acid inhibitors may be designed such that they specifically inhibit expression of an EPAS1 gene or mRNA sequence from certain species but do not inhibit expression of an EPAS1 gene or mRNA from other species. For example, a nucleic acid inhibitor useful for treatment of a pathogen infection may be designed such that it specifically inhibits an EPAS1 gene or mRNA expression in the pathogen but does not inhibit expression of an EPAS1 gene or mRNA of the host.

In certain embodiments, the subject invention provides nucleic acid inhibitors of an EPAS1 gene that are targeted to one or more specific regions within an EPAS1 gene. Exemplary regions within the human EPAS1 gene include the core target regions shown below in Table 1 (see also FIG. 1). A core target sequence generally refers to a portion of a target EPAS1 gene or corresponding mRNA which effectively inhibits EPAS1 expression upon sequence-specific binding by an inhibitor nucleic acid, such as, for example, a dsRNA, an siRNA, or an enzymatic nucleic acid. Generally, a nucleic acid inhibitor can hybridize under stringent conditions to a region of an EPAS1 protein comprising a core target sequence, or a portion of an EPAS1 gene or mRNA comprising 5, 10, or 20 nucleotides flanking one or both ends of the core target regions within the EPAS1 gene or mRNA sequence, e.g., a core target site ±5, ±10 or ±20 nucleotides at either or both ends. The core target sequences shown in Table 1 were obtained from the human EPAS1 sequence; however, the equivalent regions within EPAS1 sequences from other species, including other eukaryotes such as other mammals, are also contemplated herein.

TABLE 1

Examples of core target sequences of EPAS1 (H1F2α)

| Description | Sense Sequence | SEQ ID NO |
|---|---|---|
| EPAS1-0677 Core | 5' acacacaagcu 3' | SEQ ID NO: 2 |
| EPAS1-2894 Core | 5' gccacccagua 3' | SEQ ID NO: 3 |
| EPAS1-4999 Core | 5' ugucaacguaa 3' | SEQ ID NO: 4 | dsRNA and RNAi Constructs

In certain embodiments, the subject invention relates to double-stranded RNAs (dsRNA) and RNAi constructs. The term "dsRNA" as used herein refers to a double-stranded RNA molecule capable of RNA interference (RNAi), including siRNA (see for example, Bass, Nature 411: 428-429, 2001; Elbashir et al., Nature 411: 494-498, 2001; Kreutzer et al., PCT Publication No. WO 00/44895; Zernicka-Goetz et al., PCT Publication No. WO 01/36646; Fire, PCT Publication No. WO 99/32619; Plaetinck et al., PCT Publication No. WO 00/01846; Mello and Fire, PCT Publication No. WO 01/29058; Deschamps-Depaillette, PCT Publication No. WO 99/07409; and Li et al., PCT Publication No. WO 00/44914). In addition, RNAi is a term initially applied to a phenomenon observed in plants and worms where double-stranded RNA (dsRNA) blocks gene expression in a specific and post-transcriptional manner. RNAi provides a useful method of inhibiting or reducing gene expression in vitro or in vivo.

The term "short interfering RNA," "siRNA," or "short interfering nucleic acid," as used herein, refers to any nucleic acid capable of mediating RNAi or gene silencing when processed appropriately by a cell. For example, the siRNA can be a double-stranded polynucleotide molecule comprising self-complementary sense and antisense regions, wherein the antisense region comprises complementarity to a target gene. The siRNA can be a single-stranded hairpin polynucleotide having self-complementary sense and antisense regions, wherein the antisense region comprises complementarity to a target gene. The siRNA can be a circular single-stranded polynucleotide having two or more loop structures and a stem comprising self-complementary sense and antisense regions, wherein the antisense region comprises complementarity to a target gene, and wherein the circular polynucleotide can be processed either in vivo or in vitro to generate an active siRNA capable of mediating RNAi. The siRNA can also comprise a single-stranded polynucleotide having complementarity to a target gene, wherein the single-stranded polynucleotide can further comprise a terminal phosphate group, such as a 5'-phosphate (see for example Martinez et al., Cell 110: 563-574, 2002), or 5',3'-diphosphate. In certain embodiments, the siRNAs are non-enzymatic nucleic acids that bind to a target nucleic acid and alter the activity of the target nucleic acid. Binding and/or activity of the siRNA may be facilitated by interaction with one or more protein or protein complexes, such as the RNA Induced Silencing Complex (or RISC). In certain embodiments, the siRNAs comprise a sequence that is complementary to a target sequence along a single contiguous sequence of one strand of the siRNA molecule.

Optionally, the siRNAs of the subject invention contain a nucleotide sequence that hybridizes under physiologic conditions (e.g., in a cellular environment) to the nucleotide sequence of at least a portion of the mRNA transcript for the gene to be inhibited (the "target" gene). The double-stranded RNA need only be sufficiently similar to natural RNA that it has the ability to mediate RNAi. Thus, the subject invention has the advantage of being able to tolerate sequence variations that might be expected due to genetic mutation, strain polymorphism or evolutionary divergence. The number of tolerated nucleotide mismatches between the target sequence and the siRNA sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, 96%, 97%, 98%, or 99% sequence identity, or even 100% sequence identity, between the siRNA and the portion of the target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing).

The double-stranded structure of dsRNA may be formed by a single self-complementary RNA strand, two complementary RNA strands, or a DNA strand and a complementary RNA strand. Optionally, RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for inhibition.

As described herein, the subject siRNAs comprise a duplex region about 19-30 nucleotides in length, about 21-27 nucleotides in length, about 21-25 nucleotides in length, or about 21-23 nucleotides in length. The siRNAs are understood to recruit nuclease complexes and guide the complexes to the target gene transcript by pairing to the specific sequences. As a result, the target gene transcript is degraded by the nucleases in the protein complex. In certain embodiments, the siRNA molecules comprise a 3' hydroxyl group. In certain embodiments, the siRNA constructs can be generated, e.g., in situ, by processing longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 27 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject dsRNAs (e.g., siRNAs) can be carried out by chemical synthetic methods or by recombinant nucleic acid techniques. Endogenous RNA polymerase of the treated cell may mediate transcription in vivo, or cloned RNA polymerase can be used for transcription in vitro. As used herein, dsRNA or siRNA molecules of the subject invention need not be limited to those molecules containing only RNA, but further encompass chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al., *Nucleic Acids Res.* 25:776-780, 1997; Wilson et al., *J Mol. Recog.* 7:89-98, 1994; Chen et al., *Nucleic Acids Res.* 23:2661-2668, 1995; Hirschbein et al., *Antisense Nucleic Acid Drug Dev.* 7:55-61, 1997). Merely to illustrate, the backbone of a dsRNA or siRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the subject invention lack 2'-hydroxy (2'-OH) containing nucleotides. In certain embodiments, the siRNA molecules comprise a phosphorothioate sense strand. In certain embodiments, the siRNA molecules comprise a phosphodiester antisense strand.

In a specific embodiment, at least one strand of the siRNA molecules has a 3' overhang from about 1 to about 10 nucleotides in length, about 1 to 5 nucleotides in length, about 1 to 3 nucleotides in length, or about 2 to 4 nucleotides in length. In certain embodiments, an siRNA may comprise one strand having a 3' overhang and the other strand is blunt-ended at the 3' end (e.g., does not have a 3' overhang). In another embodiment, an siRNA may comprise a 3' overhang on both strands. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In a further specific embodiment, the dsRNA or siRNA is in the form of a hairpin structure (or hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev.* 16:948-58,2002; McCaffrey et al., *Nature* 418:38-9, 2002; McManus et al., *RNA* 8:842-50, 2002; Yu et al., *Proc. Natl. Acad. Sci. U.S.A.* 99:6047-6052, 2002. Preferably, such hairpin RNAs are engineered in cells or in an animal to ensure continuous and stable suppression of a target gene. It is known in the art that siRNAs can be produced by processing a hairpin RNA in the cell.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for a dsRNA of interest, wherein the two overlapping transcription units yield both sense and antisense RNA transcripts from the same transgene fragment in a host cell.

In exemplary embodiments, the subject invention provides siRNAs directed to a core target sequence as shown above in Table 1, or a region corresponding to a region of an EPAS1 gene or mRNA corresponding to a core target sequence with ±5, ±10, or ±20 nucleotides flanking the core target sequence on one or both sides. The sequences of a variety of exemplary siRNA duplexes are provided below in Tables 2-6.

TABLE 2

Examples of siRNA duplexes directed to target sites A, B and C.
Underlined residues represent 3' overhangs.

| Description | Sequence | Strand | SEQ ID NO |
|---|---|---|---|
| siEPAS1A (or EPAS1-0677) | 5' ugcgaacacacaagcuccu<u>cu</u> 3'<br>3' <u>gg</u>acgcuugugugguucgagga 5' | Sense<br>Antisense | SEQ ID NO: 5<br>SEQ ID NO: 6 |
| siEPAS1B (or EPAS1-2894) | 5' gcuacgccacccaguacca<u>gg</u> 3'<br>3' <u>ca</u>cgaugcgguggguucauggu 5' | Sense<br>Antisense | SEQ ID NO: 7<br>SEQ ID NO: 8 |
| siEPAS1C (or EPAS1-4999) | 5' cuaccugucaacguaacga<u>uu</u> 3'<br>3' <u>gg</u>gauggacaguugcauugcu 5' | Sense<br>Antisense | SEQ ID NO: 9<br>SEQ ID NO: 10 |

The corresponding 27 mer siRNAs of the three 21 mers above are also provided. More specifically, the "27R" and "27L" variants may be more potent in down-regulating EPAS1 expression. See Kim et al., *Nature Biotechnology* 23:222-226, 2005; Rose et al., *Nucleic Acids Research* 33(13):4140-56, Jul. 26, 2005). The 'R' 27 mer has added bases extending to the right side of the initial target sequence (3' with respect to the target), while the 'L' 27 mer has added bases extending to the left side of the initial target sequence (5' with respect to the target). Examples of the 27 mer siRNAs are shown in Table 3 below.

TABLE 3

27 mer siRNAs corresponding to the 21 mer siRNAs shown in Table 2 above.
UPPERCASE letters denote DNA residues, lowercase letters denote RNA residues,
and [5' phos] denotes a 5' phosphate.

| Description | Sequence | Strand | SEQ ID NO |
|---|---|---|---|
| siEPAS1A1 (or EPAS1-0677-27R) | 5' [5'phos]ugcgaacacacaagcuccucuccTC 3'<br>3' ggacgcuugugugguucgaggagaggag 5' | Sense<br>Antisense | SEQ ID NO: 11<br>SEQ ID NO: 12 |
| siEPAS1A2 (or EPAS1-0677-27L) | 5' gcuuccugcgaacacacaagcuccucu 3'<br>3' CGaaggacgcuugugugguucgagga [5'phos] 5' | Sense<br>Antisense | SEQ ID NO: 13<br>SEQ ID NO: 14 |
| siEPAS1B1 (or EPAS1-2894-27R) | 5' [5'phos] gcuacgccacccaguaccaggacTA 3'<br>3' cacgaugcgguggucauggaccugau 5' | Sense<br>Antisense | SEQ ID NO: 15<br>SEQ ID NO: 16 |
| siEPAS1B2 (or EPAS1-2894-27L) | 5' cacagugcuacgccacccaguaccagg 3'<br>3' GTgucacgaugcgguggucauggu [5'phos] 5' | Sense<br>Antisense | SEQ ID NO: 17<br>SEQ ID NO: 18 |
| siEPAS1C1 (or EPAS1-4999-27R) | 5' [5'phos] cuaccugucaacguaacgauuucAT 3'<br>3' gggauggacaguugcauugcuaaagua 5' | Sense<br>Antisense | SEQ ID NO: 19<br>SEQ ID NO: 20 |
| siEPAS1C2 (or EPAS1-4999-27L) | 5' uuaaccuaccugucaacguaacgauu 3'<br>3' aauugggauggacaguugcauugcu [5'phos] 5' | Sense<br>Antisense | SEQ ID NO: 21<br>SEQ ID NO: 22 |

The subject invention also provides siRNAs that target within −20 to +20 bases of a core target sequence or within −10 to +10 bases of an siRNA of the subject invention. For example, 21 mer duplexes having target sites within −5 to +5 bases of each of the three 2 mer siRNAs are shown or −10 to +10 bases of each of the three core target sequences) are shown in Tables 4-6 below.

TABLE 4 siRNA duplexes directed against target site A and tiled from
−5 to +5 bases of the siEPAS1A siRNA diplex
Underlined residues represent 3' overhangs.

| Description | Sequence | Stand | SEQ ID NO |
|---|---|---|---|
| siEPAS1A-5 (or EPAS1-0672) | 5' cuuccugcgaacacacaag<u>cu</u> 3'<br>3' <u>uc</u>gaaggacgcuugugguuc 5' | Sense<br>Antisense | SEQ ID NO: 23<br>SEQ ID NO: 24 |

TABLE 4-continued siRNA duplexes directed against target site A and tiled from
-5 to +5 bases of the siEPAS1A siRNA diplex
Underlined residues represent 3' overhangs.

| Description | Sequence | Stand | SEQ ID NO |
|---|---|---|---|
| siEPAS1A-4 (or EPAS1-0673) | 5' uuccugcgaacacacaagcuc 3'<br>3' cgaaggacgcuugugudguucg 5' | Sense<br>Antisense | SEQ ID NO: 25<br>SEQ ID NO: 26 |
| siEPAS1A-3 (or EPAS1-0674) | 5' uccugcgaacacacaagcucc 3'<br>3' gaaggacgcuuguguguucga 5' | Sense<br>Antisense | SEQ ID NO: 27<br>SEQ ID NO: 28 |
| siEPAS1A-2 (or EPAS1-0675) | 5' ccugcgaacacacaagcuccu 3'<br>3' aaggacgcuuguguguucgag 5' | Sense<br>Antisense | SEQ ID NO: 29<br>SEQ ID NO: 30 |
| siEPAS1A-1 (or EPAS1-0676) | 5' cugcgaacacacaagcuccuc 3'<br>3' aggacgcuuguguguucgagg 5' | Sense<br>Antisense | SEQ ID NO: 31<br>SEQ ID NO: 32 |
| siEPAS1A + 1 (or EPAS1-0678) | 5' gcgaacacacaagcuccucuc 3'<br>3' gacgcuuguguguucgaggag 5' | Sense<br>Antisense | SEQ ID NO: 33<br>SEQ ID NO: 34 |
| siEPAS1A + 2 (or EPAS1-0679) | 5' cgaacacacaagcuccucucc 3'<br>3' acgcuuguguguucgaggaga 5' | Sense<br>Antisense | SEQ ID NO: 35<br>SEQ ID NO: 36 |
| siEPAS1A + 3 (or EPAS1-0680) | 5' gaacacacaagcuccucuccu 3'<br>3' cgcuuguguguucgaggagag 5' | Sense<br>Antisense | SEQ ID NO: 37<br>SEQ ID NO: 38 |
| siEPAS1A + 4 (or EPAS1-0681) | 5' aacacacaagcuccucuccuc 3'<br>3' gcuuguguucgaggagagg 5' | Sense<br>Antisense | SEQ ID NO: 39<br>SEQ ID NO: 40 |
| siEPAS1A + 5 (or EPAS1-0682) | 5' acacacaagcuccucuccuca 3'<br>3' cuuguguguucgaggagagga 5' | Sense<br>Antisense | SEQ ID NO: 41<br>SEQ ID NO: 42 |

TABLE 5 siRNA duplexes directed against target site B and tiled from
-5 to +5 bases of the siEPAS1B siRNA diplex
Underlined residues represent 3' overhangs.

| Description | Sequence | Stand | SEQ ID NO |
|---|---|---|---|
| siEPAS1B-5 (or EPAS1-2889) | 5' acagugcuacgccacccagua 3'<br>3' ggugucacgaugcgguggguc 5' | Sense<br>Antisense | SEQ ID NO: 43<br>SEQ ID NO: 44 |
| siEPAS1B-4 (or EPAS1-2890) | 5' cagugcuacgccacccaguac 3'<br>3' gugucacgaugcggugggguca 5' | Sense<br>Antisense | SEQ ID NO: 45<br>SEQ ID NO: 46 |
| siEPAS1B-3 or EPAS1-2891) | 5' agugcuacgccacccaguacc 3'<br>3' ugucacgaugcggugggucau 5' | Sense<br>Antisense | SEQ ID NO: 47<br>SEQ ID NO: 48 |
| siEPAS1B-2 (or EPAS1-2892) | 5' gugcuacgccacccaguacca 3'<br>3' gucacgaugcggugggucaug 5' | Sense<br>Antisense | SEQ ID NO: 49<br>SEQ ID NO: 50 |
| siEPAS1B-1 (or EPAS1-2893) | 5' ugcuacgccacccaguaccag 3'<br>3' ucacgaugcggugggucaugg 5' | Sense<br>Antisense | SEQ ID NO: 51<br>SEQ ID NO: 52 |
| siEPAS1B + 1 (or EPAS1-2895) | 5' cuacgccacccaguaccagga 3'<br>3' acgaugcggugggucaugguc 5' | Sense<br>Antisense | SEQ ID NO: 53<br>SEQ ID NO: 54 |
| siEPAS1B + 2 (or EPAS1-2896) | 5' uacgccacccaguaccaggac 3'<br>3' cgaugcggugggucauggucc 5' | Sense<br>Antisense | SEQ ID NO: 55<br>SEQ ID NO: 56 |
| siEPAS1B + 3 (or EPAS1-2897) | 5' acgccacccaguaccaggacu 3'<br>3' gaugcggugggucauggaccu 5' | Sense<br>Antisense | SEQ ID NO: 57<br>SEQ ID NO: 58 |
| siEPAS1B + 4 (or EPAS1-2898) | 5' cgccacccaguaccaggacua 3'<br>3' augcggugggucaugguccug 5' | Sense<br>Antisense | SEQ ID NO: 59<br>SEQ ID NO: 60 |
| siEPAS1B + 5 (or EPAS1-2899) | 5' gccacccaguaccaggacuac 3'<br>3' ugcggugggucaugguccuga 5' | Sense<br>Antisense | SEQ ID NO: 61<br>SEQ ID NO: 62 |

TABLE 6 siRNA duplexes directed against target site C and tiled from
−5 to +5 bases of the siEPAS1C siRNA diplex
Underlined residues represent 3' overhangs.

| Description | Sequence | Stand | SEQ ID NO |
|---|---|---|---|
| siEPAS1C-5 (or EPAS1-4994) | 5' uaacccuaccugucaacgu<u>aa</u> 3'<br>3' <u>ua</u>auugggauggacaguugca 5' | Sense<br>Antisense | SEQ ID NO: 63<br>SEQ ID NO: 64 |
| siEPAS1C-4 (or EPAS1-4995) | 5' aacccuaccugucaacgu<u>ac</u> 3'<br>3' <u>aa</u>uugggauggacaguugcau 5' | Sense<br>Antisense | SEQ ID NO: 65<br>SEQ ID NO: 66 |
| siEPAS1C-3 (or EPAS1-4996) | 5' acccuaccugucaacgua<u>cg</u> 3'<br>3' <u>au</u>ugggauggacaguugcauu 5' | Sense<br>Antisense | SEQ ID NO: 67<br>SEQ ID NO: 68 |
| siEPAS1C-2 (or EPAS1-4997) | 5' cccuaccugucaacguac<u>ga</u> 3'<br>3' <u>uu</u>gggauggacaguugcauug 5' | Sense<br>Antisense | SEQ ID NO: 69<br>SEQ ID NO: 70 |
| siEPAS1C-1 (or EPAS1-4998) | 5' ccuaccugucaacguacg<u>au</u> 3'<br>3' <u>ug</u>ggauggacaguugcauugc 5' | Sense<br>Antisense | SEQ ID NO: 71<br>SEQ ID NO: 72 |
| siEPAS1C + 1 (or EPAS1-5000) | 5' uaccugucaacguaacgau<u>uu</u> 3'<br>3' <u>gg</u>auggacaguugcauugcua 5' | Sense<br>Antisense | SEQ ID NO: 73<br>SEQ ID NO: 74 |
| siEPAS1C + 2 (or EPAS1-5001) | 5' accugucaacguaacgauu<u>uc</u> 3'<br>3' <u>ga</u>uggacaguugcauugcuaa 5' | Sense<br>Antisense | SEQ ID NO: 75<br>SEQ ID NO: 76 |
| siEPAS1C + 3 (or EPAS1-5002) | 5' ccugucaacguaacgauuu<u>ca</u> 3'<br>3' <u>au</u>ggacaguugcauugcuaaa 5' | Sense<br>Antisense | SEQ ID NO: 77<br>SEQ ID NO: 78 |
| siEPAS1C + 4 (or EPAS1-5003) | 5' cugucaacguaacgauuuc<u>au</u> 3'<br>3' <u>ug</u>gacaguugcauugcuaaag 5' | Sense<br>Antisense | SEQ ID NO: 79<br>SEQ ID NO: 80 |
| siEPAS1C + 5 (or EPAS1-5004) | 5' ugucaacguaacgauuuca<u>ug</u> 3'<br>3' <u>gg</u>acaguugcauugcuaaagu 5' | Sense<br>Antisense | SEQ ID NO: 81<br>SEQ ID NO: 82 |

Enzymatic Nucleic Acids

In certain embodiments, the subject invention relates to enzymatic nucleic acids that inhibit an EPAS1 gene or mRNA expression. Exemplary enzymatic nucleic acids include those that are targeted to one of the core target sequences provided in Table 1 above, or a region comprising a core target sequence with 5, 10, or 20 nucleotides flanking one or both sides of the core target sequences. By "enzymatic nucleic acid," it is meant a nucleic acid which has complementarity in a substrate binding region to a specified target gene, and also has an enzymatic activity which is active to specifically cleave a target nucleic acid. It is understood that the enzymatic nucleic acid is able to intermolecularly cleave a nucleic acid and thereby inactivate a target nucleic acid. These complementary regions allow sufficient hybridization of the enzymatic nucleic acid to the target nucleic acid and thus permit cleavage. One hundred percent complementarity (identity) is preferred, but complementarity as low as 50-75% can also be useful in this application (see for example Werner and Uhlenbeck, *Nucleic Acids Research* 23: 2092-2096, 1995; Hammann et al., *Antisense and Nucleic Acid Drug Dev.* 9: 25-31, 1999). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these termologies describe nucleic acids with enzymatic activity. The specific enzymatic nucleic acids described herein are not limited in application and those skilled in the art will recognize that all that is important in an enzymatic nucleic acid of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., *JAMA* 260:3030, 1988).

Several varieties of naturally-occurring enzymatic nucleic acids are currently known. Each can catalyze the hydrolysis of nucleic acid phosphodiester bonds in trans (and thus can leave other nucleic acids) under physiological conditions. In general, enzymatic nucleic acids act by first binding to a target nucleic acid. Such binding occurs through the target binding portion of an enzymatic nucleic acid which is held in close proximity to an enzymatic portion of the molecule that acts to cleave the target nucleic acid. Thus, the enzymatic nucleic acid first recognizes and then binds a target nucleic acid through complementary base-pairing, and once bound to the correct site, acts enzymatically to cut the target nucleic acid. Strategic cleavage of such a target nucleic acid will destroy its ability to direct synthesis of an encoded protein. After an enzymatic nucleic acid has bound and cleaved its nucleic acid target, it is released from that nucleic acid to search for another target and can repeatedly bind and cleave new targets.

In a specific embodiment, the subject enzymatic nucleic acid is a ribozyme designed to catalytically cleave an EPAS1 mRNA to prevent its translation (see, e.g., PCT International Publication WO90/11364, published Oct. 4, 1990; Sarver et al., *Science* 247:1222-1225, 1990; and U.S. Pat. No. 5,093, 246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNAs have the following sequence of two bases: 5'-UG-3'. The construction and production of hammerhead ribozymes is well known in the art and is described more fully in Haseloff and Gerlach, 1988, Nature, 334:585-591. The ribozymes of the present invention also include RNA endoribonucleases (hereinafter "Cech-type ribozymes") such as the one which occurs naturally in *Tetrahymena thermophila* (known as the IVS or L-19 IVS RNA) and which has been extensively described (see, e.g., Zaug, et al., *Science* 224:574-578, 1984; Zaug and Cech, *Science* 231:470-475, 1986; Zaug, et al., *Nature,* 324:429-433, 1986; published International patent application No. WO88/04300 by University Patents Inc.; Been and Cech, *Cell* 47:207-216, 1986).

In another specific embodiment, the subject enzymatic nucleic acid is a DNA enzyme. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. Briefly, to design an ideal DNA enzyme that specifically recognizes and cleaves a target nucleic acid, one of skill in the art must first identify the unique target sequence. Preferably, the unique or substantially unique sequence is a G/C rich of approximately 18 to 22 nucleotides. High G/C content helps insure a stronger interaction between the DNA enzyme and the target gene sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

In certain embodiments, the nucleic acid agents of the subject invention can be between 12 and 200 nucleotides in length. In one embodiment, exemplary enzymatic nucleic acids of the subject invention are between 15 and 50 nucleotides in length, including, for example, between 25 and 40 nucleotides in length (for example see Jarvis et al., *J. Biol. Chem.* 271: 29107-29112, 1996). In another embodiment, exemplary antisense molecules of the subject invention are between 15 and 75 nucleotides in length, including, for example, between 20 and 35 nucleotides in length (see for example Woolf et al., *PNAS* 89: 7305-7309, 1992; Milner et al., *Nature Biotechnology* 15: 537-541, 1997). In another embodiment, exemplary siRNAs of the subject invention are between 20 and 30 nucleotides in length, including, for example, between 21 and 27 nucleotides in length. Those skilled in the art will recognize that all that is required is that the subject nucleic acid agent be of length and conformation sufficient and suitable for its activity contemplated herein. The length of the nucleic acid agents of the instant invention is not limited within the general limits stated.

Synthesis of Nucleic Acid Agents

Synthesis of nucleic acids greater than 100 nucleotides in length is difficult using automated methods, and the therapeutic cost of such molecules is prohibitive. For the present invention, small nucleic acid motifs (small refers to nucleic acid motifs less than about 100 nucleotides in length, preferably less than about 80 nucleotides in length, and more preferably less than about 50 nucleotides in length (e.g., enzymatic nucleic acids and RNAi constructs) are preferably used for exogenous delivery. The simple structure of these molecules increases the ability of the nucleic acid to invade targeted regions of RNA structure.

Exemplary nucleic acid inhibitor molecules, including RNA and DNA molecules, of the instant invention can be chemically synthesized. To illustrate, oligonucleotides (e.g., DNA) are synthesized using protocols known in the art as described in Caruthers et al., *Methods in Enzymology* 211: 3-19, 1992; Thompson et al., International PCT Publication No. WO 99/54459, Wincott et al., *Nucleic Acids Res.* 23: 2677-2684, 1995; Wincott et al., *Methods Mol. Bio.* 74:59, 1997; Brennan et al., *Biotechnol Bioeng.* 61: 33-45, 1998; and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer with a 2.5 min coupling step for 2'-O-methylated nucleotides and a 45 sec coupling step for 2'-deoxy nucleotides. Alternatively, syntheses can be performed on a 96-well plate synthesizer, such as the instrument produced by Protogene (Palo Alto, Calif.) with minimal modification to the cycle.

Optionally, portions of the instant nucleic acids can be synthesized separately and joined together post-synthetically, for example by ligation (Moore et al., *Science* 256: 9923, 1992; Draper et al., International PCT publication No. WO 93/23569; Shabarova et al., *Nucleic Acids Research* 19: 4247, 1991; Bellon et al., *Nucleosides & Nucleotides* 16: 951, 1997; Bellon et al., *Bioconjugate Chem.* 8: 204, 1997).

Preferably, the nucleic acids herein are modified extensively to enhance stability by modification with nuclease resistant groups, for example, 2'-amino, 2'-C-allyl, 2'-flouro, 2'-O-methyl, 2'-H (for a review see Usman and Cedergren, *TIBS* 17:34, 1992; Usman et al., *Nucleic Acids Symp. Ser.* 31: 163, 1994). Ribozymes are purified by gel electrophoresis using general methods or are purified by high pressure liquid chromatography (HPLC; See Wincott et al., supra) and are re-suspended in water.

Optimizing Activity and Design of the Nucleic Acids

Nucleic acids with modifications (e.g., base, sugar and/or phosphate) can prevent their degradation by serum ribonucleases and thereby increase their potency. There are several examples in the art describing sugar, base and phosphate modifications that can be introduced into nucleic acids with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, *TIBS* 17: 34, 1992; Usman et al., *Nucleic Acids Symp. Ser.* 31:163, 1994; Burgin et al., *Biochemistry* 35: 14090, 1996). Sugar modifications of nucleic acids have been extensively described in the art (see Eckstein et al., PCT Publication No. WO 92/07065; Perrault et al., *Nature* 344: 565-568, 1990; Pieken et al., *Science* 253: 314-317, 1991; Usman and Cedergren, *Trends in Biochem. Sci.* 17: 334-339, 1992; Usman et al. PCT Publication No. WO 93/15187; Sproat, U.S. Pat. No. 5,334, 711 and Beigelman et al., *J. Biol. Chem.,* 270:25702, 1995; Beigelman et al., PCT publication No. WO 97/26270; Beigelman et al., U.S. Pat. No. 5,716,824; Usman et al., U.S. Pat. No. 5,627,053; Woolf et al., PCT Publication No. WO 98/13526; Thompson et al., U.S. Ser. No. 60/082,404 which was filed on Apr. 20, 1998; Karpeisky et al., *Tetrahedron Lett.,* 39:1131, 1998; Earnshaw and Gait, *Biopolymers (Nucleic acid Sciences)* 48:39-55, 1998; Venna and Eckstein, *Annu. Rev. Biochem.* 67:99-134, 1998; and Burlina et al., *Bioorg. Med. Chem.* 5: 1999-2010, 1997). Similar modifications can be used to modify the nucleic acids of the instant invention.

While chemical modification of oligonucleotide internucleotide linkages with phosphorothioate, phosphorothioate, and/or 5'-methylphosphonate linkages improves stability, an over-abundance of these modifications can cause toxicity. Therefore, the amount of these internucleotide linkages should be evaluated and appropriately minimized when designing the nucleic acids. The reduction in the concentration of these linkages should lower toxicity resulting in increased efficacy and higher specificity of these molecules.

In one embodiment, nucleic acids of the invention include one or more G-clamp nucleotides. A G-clamp nucleotide is a modified cytosine analog wherein the modifications confer the ability to hydrogen bond both Watson-Crick and Hoogsteen faces of a complementary guanine within a duplex (see for example, Lin and Matteucci, J. Am. Chem. Soc. 120:8531-8532, 1998). A single G-clamp analog substitution within an oligonucleotide can result in substantially enhanced helical thermal stability and mismatch discrimination when hybridized to complementary oligonucleotides. The inclusion of such nucleotides in nucleic acids of the invention results in both enhanced affinity and specificity to nucleic acid targets. In another embodiment, nucleic acids of the invention include one or more LNA (locked nucleic acid) nucleotides such as a 2', 4'-C mythylene bicyclo nucleotide (see for example Wengel et al., PCT Publication Nos. WO 00/66604 and WO 99/14226).

In another embodiment, the invention features conjugates and/or complexes of nucleic acids targeting an EPAS1 gene. Such conjugates and/or complexes can be used to facilitate delivery of nucleic acids into a biological system, such as cells. The conjugates and complexes provided by the instant invention can impart therapeutic activity by transporting or transferring therapeutic agents to a target tissue or cell type, across cellular membranes, altering the pharmacokinetics, and/or modulating the localization of nucleic acids of the invention. Such conjugates and/or complexes are also described below.

The present invention encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multicomponent system, with or without degradable linkers. These compounds are expected to improve delivery and/or localization of nucleic acids of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable nucleic acid linker molecule" as used herein, refers to a nucleic acid molecule that is designed as a biodegradable linker to connect one molecule to another molecule, for example, a biologically active molecule. The stability of the biodegradable nucleic acid linker molecule can be modulated by using various combinations of ribonucleotides, deoxyribonucleotides, and chemically modified nucleotides, for example, 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus based linkage, for example, a phosphoramidate or phosphodiester linkage. The biodegradable nucleic acid linker molecule can also comprise nucleic acid backbone, nucleic acid sugar, or nucleic acid base modifications. The term "biodegradable" as used herein, refers to degradation in a biological system, for example enzymatic degradation or chemical degradation.

Therapeutic nucleic acid agents, such as the molecules described herein, delivered exogenously are optimally stable within cells until translation of the target RNA has been inhibited long enough to reduce the levels of the undesirable protein. This period of time varies between hours to days depending upon the disease state. These nucleic acid agents should be resistant to nucleases in order to function as effective intracellular therapeutic agents. Improvements in the chemical synthesis of nucleic acids herein and in the art have expanded the ability to modify nucleic acids by introducing nucleotide modifications to enhance their nuclease stability as described above.

In another aspect the nucleic acids comprise a 5'- and/or a 3'-cap structure. By "cap structure," it is meant chemical modifications, which have been incorporated at either terminus of the oligonucleotide (see for example Wincott et al., WO 97/26270). These terminal modifications protect the nucleic acid from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al, supra). In other non-limiting examples, the 3'-cap includes, for example, 4',5'-methylene nucleotide; 1-(bela-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threopentofuranosy nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, Tetrahedron 49:1925, 1993).

siRNA Design

RNA interference, or RNAi, is a gene silencing mechanism originally described in plants (where it was known as post-transcriptional gene silencing, or PTGS), C. elegans and Drosophila (reviewed in Bernstein et al., 2001; Carmell et al., 2002). In the current model, the RNAi pathway is activated by a double-stranded RNA (dsRNA) "trigger" that is then processed into short, 21-23 nucleotide dsRNAs referred to as small interfering RNAs (siRNAs) by the cellular enzyme Dicer. The siRNAs become incorporated into the RNA-induced silencing complex (RISC), where the siRNA antisense strand serves as a guide to target the homologous mRNA for endonucleolytic cleavage within the siRNA/target duplex, approximately 10 bases from the 5' end of the siRNA guide. In mammalian cells, dsRNA longer than 30 nucleotides triggers the nonspecific interferon pathway rather than RNAi. However, Tuschl and colleagues demonstrated (Elbashir et al., 2001a; Harborth et al., 2001; Caplen et al., 2002) that shorter siRNAs exogenously introduced into mammalian cells bypass the Dicer step and directly activate homologous mRNA degradation, without initiating the interferon response. Subsequently, a number of labs demonstrated the feasibility of expressing siRNAs and the related short hairpin RNAs (shRNAs) in vivo against human viral and cellular targets. Advances in RNAi are rapidly expanding and considerable progress has already been made toward therapeutic applications (Zamore, 2001; Kitabwalla and Ruprecht, 2002; Martinez et al., 2002; Couzin, 2003; Scherr et al., 2003; Wilson et al., 2003; Hannon and Rossi, 2004).

Synthetic siRNAs are the method of choice for exogenous, short-term applications. Currently, unmodified siRNAs mediate RNAi effects that typically peak at 2-3 days post-transfection. The most common design for synthetic siRNAs mimics the endogenous siRNAs produced by Dicer cleavage of trigger dsRNA (Elbashir et al., 2001a), where the sense and antisense strands are 21-23 nucleotides long. The annealed portion of the duplex is completely complementary, except for two nucleotide overhangs at both 3' ends. For synthetic siRNAs, the 3' dinucleotide overhangs can be derived from the target sequence, as in their natural counterparts. While siRNAs constructed from 21-23-mers are sufficient for most purposes, oligomers of up to 29 nucleotides can be used without initiating the interferon response. We have observed that siRNAs that are produced from longer double-stranded RNAs in cells by the action of Dicer can be up to 100 times more potent than a 21 mer provided exogenously (Kim et al., 2005). A companion manuscript by Siolas et al. (2005) showed a similar conclusion, although these investigators used synthetic hairpins as Dicer substrates. The studies proposed here will capitalize upon these important findings for generating potent siRNAs for use in animal studies. New design rules will be discussed that enable the exact prediction of the siRNA that will be generated from the Dicer substrate duplex RNAs are discussed next.

Mismatches between the siRNA antisense strand and the target tend to reduce activity to varying degrees depending on their number and location. While the rules governing the relationship between siRNA/target mismatch and RNAi activity have not been fully worked out, some generalizations can be made that probably apply to both siRNAs and simple shRNAs. Mutations near the endonucleolytic cleavage site frequently, but not always, reduce the RNAi effect. Also, mutations in the first half of the antisense strand (5' end) are very detrimental (Randall and Rice, 2001; Holen et al., 2002; Amarzguioui et al., 2003). Since endonucleolytic cleavage is 'measured' from the 5' end of the antisense siRNA strand, it is possible that mutations in the 5' end of the guide strand destabilize the antisense/mRNA target duplex in the activated RISC complex, inhibiting cleavage. Taken together, these results imply that, when designing RNAi constructs to target a specific isoform, it may be advisable to select a target site in the target isoform, such that mismatches between its corresponding siRNA and the non-targeted isoform fall in the 5' end of the duplex. If this is not possible, as when the target is inaccessible to cleavage (reviewed in Scherer and Rossi, 2003b), it is important to test for cross-reactivity.

While siRNAs constructed from 21-23-mers are sufficient for most purposes, oligomers of up to 29 nucleotides can be used without initiating the interferon effects. We have observed that siRNAs that are produced from longer double-stranded RNAs in cells by the action of Dicer can be up to 100 times more potent than a 21 mer provided exogenously (Kim et al., 2005). A companion manuscript by Siolas et al. (2005) describes a similar conclusion, although these investigators used synthetic hairpins as Dicer substrates. The proposed studies will capitalize upon these important findings for generating potent siRNAs for use in animal studies. New design rules will be discussed that enable the exact prediction of the siRNA that will be generated from the Dicer substrate duplex RNAs.

Experiments in *Drosophila* embryo lysates indicated a need for either free 5'-OH or 5'-phosphate on synthetic siRNA strands (Elbashir et al., 2001b; Nykanen et al., 2001). Similar results were observed in HeLa extracts (Schwarz et al., 2002) or intact cells (Chiu and Rana, 2002). Asymmetric 5'-amino modification of one or the other siRNA strand showed that 5' amino modification of the antisense strand abolishes RNAi while the same modification of only the sense strand does not inhibit the RNAi effect. Also, non-phosphorylated synthetic siRNAs transfected into cells and later re-isolated cannot be phosphorylated by kinase in vitro unless pretreated with a phosphatase (Chiu and Rana, 2002). Taken together, this suggests a strong requirement in vitro for a 5' phosphate on the antisense strand. This is consistent with the hypothesis that modifications of this nucleotide interfere with the ability of the antisense strand to serve as a guide for endonucleolytic cleavage in the activated RISC complex. On the other hand, modifications blocking the 3' end have little effect on duplex siRNA, on either strand in most cases (Amarzguioui et al., 2003).

Studies of backbone modifications on siRNA duplexes have revealed that up to six, 2'-O-methyls per siRNA strand distributed between the 5' and 3' termini, or two, 2'-O-allyl modifications at the 3' termini do not adversely affect RNAi (Amarzguioui et al., 2003). Increasing the number of modifications beyond this point, or allyl modification of the 5' termini, reduce RNAi (Amarzguioui et al., 2003; Holen et al., 2003). Conversely more than two phosphorothioate modifications are cytotoxic, while not promoting significant increases in potency (Amarzguioui et al., 2003). The advantage of backbone modifications on siRNAs may only be realized when the siRNAs are directly injected into animals, since the backbone modifications prolong the half-lives of these molecules (Layzer et al., 2004; Soutschek et al., 2004). Here, we will take advantage of the protection from serum nucleases afforded by cyclodextrin nano-particle carriers and therefore our RNAs will not be backbone modified so they can be effectively Diced in vivo.

Definition of the Sequence

RNAi can be triggered either by synthetic siRNAs delivered to cells using cationic lipids or other carriers, or via gene expression of 21 mer sense and antisense strands or short hairpin RNAs that get processed into siRNAs (reviewed in Scherer and Rossi, 2003a). An important determinant for the success of siRNA mediated knockdown is the combination of target site accessibility and the selection of the appropriate strand from the siRNA. We and others have developed algorithms to identify an appropriate combination of target site and siRNA duplex (Heale et al., 2005). Our algorithm takes into account target site secondary structure predictions and the duplex end stability of the siRNA. The latter is important in the selection of the antisense strand into RISC (Khvorova et al., 2003; Schwarz et al., 2003; Tomari et al., 2004). It has also been discovered that dsRNAs that are long enough to be cleaved the RNAse III family member Dicer can be up to 100 times more potent than 21 mer siRNAs (Kim et al., 2005; Siolas et al., 2005). Thus, our preferred method for identification of target sites and siRNAs is to pick sequence motifs with our algorithm (Heale et al., 2005), identify potential target sequences and the 21 mer siRNAs and test several 21 mers for relative efficacy.

A novel computational algorithm for determination of optimal target sites was used to identify three potential target sites within the human endothelial PAS domain protein 1 (EPAS1) gene. siRNAs directed to these three target sequences were synthesized and tested in the cell extract prescreen assay as described by Davis et al. in US 2006/0263435 A1, hereby incorporated by reference in its entirety.

It has previously been demonstrated that a cell extract binding assay is highly predictive of intracellular efficacy (see, e.g., U.S. Pat. No. 7,427,605, incorporated herein in its entirety). Briefly, synthetic 21 mers are labeled at their 5' termini with $^{32}$P and incubated in HEK 293 cytoplasmic extracts at room temperature. The siRNAs can be bound in a complex that contains the RISC component argonaute 2 (Ago2). The binding efficacy correlates strongly with intracellular potency, as demonstrated in FIG. 6 of U.S. Pat. No. 7,427,605. Once the most potent 2 mer is identified, that sequence is incorporated into a 27-base duplex which is a substrate for Dicer. A format for Dicing has been established such that only the 21 mer of choice is produced from the 27 mer (see below). Thus, the only constraint on using the chosen 27 mer is delivery. The preferred substrate for in vivo Dicing has the following general characteristics:

```
5 ' NNNNNNNNNNNNNNNNNNNNNNNNNdNdN3 '

3 ' NNNNNNNNNNNNNNNNNNNNNNNNNNNNN5 '
```

Using in vitro Dicing and mass spec analyses of the Diced products it has been determined that Dicer recognizes the 2 base three prime overhang, and cleaves 21 bases from the 5' end of the sense strand, and 21 bases from the 2 base overhang to generate only one 21 mer. By including two deoxyribonucleotides at the 3' end of the sense strand (dN), Dicer does not come in from the right hand side of this duplex, thus ensuring generation of only the 21 mer of interest. FIG. 6 and Example 1 of U.S. Pat. No. 7,427,605 presents representative results of an extract binding assay in which a series of 21 mers differing by a single base, are incubated with the extracts. The binding affinity of the siRNAs is precisely correlated with the knockdown of the target. This assay has been repeated for over 20 different siRNAs, and the correlation remains.

The human EPAS1 mRNA sequence was run through the algorithm as described in Heale et al., 2005. The top several predicted siRNAs and targets were analyzed for potential complementarity with other human sequences, watching for extended matches at the 5' end of the antisense strand. The sequences that did not share extended 5' homology for other targets were tested at a concentration of 10 nM. The dsRNAs exhibiting the most significant reduction of EPAS1 mRNA levels and/or anti-proliferative effect in A498 cells may be used in subsequent in vivo experiments.

Use of the EPAS1 Inhibitors

In certain embodiments, the present invention provides methods of inhibiting unwanted proliferation of one or more cells, for example, tumor or cancerous cells, or pathogen cells. In certain embodiments, the invention provides methods of inhibiting or reducing tumor growth and methods of treating an individual suffering from a cancer. These methods involve administering to the individual patient an effective amount of one or more EPAS1 inhibitors (e.g., siRNAs) as described above. In certain embodiments, the present invention provides methods for treating metastatic cancer and/or preventing metastasis. In certain embodiments, the present invention provides methods for treating cancer resistant to traditional therapies, such as, for example chemotherapeutic agents. Certain methods are particularly aimed at therapeutic and prophylactic treatments of animals, and more particularly, humans, and in such methods, a therapeutically effective amount of the EPAS1 inhibitor(s) is administered to the animal or human patient.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As described herein, the tumor or cancer includes a tumor inside an individual, a tumor xenograft, or a tumor cultured in vitro. In particular, nucleic acid agents of the present invention are useful for treating or preventing a cancer. Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the EPAS1 inhibitors of the present invention include cancers comprising hedgehog-expressing cells. Still further exemplary forms of cancer which can be treated with an EPAS1 inhibitor of the present invention include cancers comprising EPAS1-expressing cells. In certain such embodiments, the normal or non-cancerous cells of the same tissue type as the cancer cells may not express EPAS1 at a level detectable by techniques in the art; for example, normal renal tissue or renal cells do not express detectable levels of EPAS1, in contrast to expression of EPAS1 in renal carcinoma cells. The present invention contemplates that the EPAS1 inhibitors herein can be used alone, or can be administered as part of an overall treatment regimen including other therapeutics and/or other traditional or non-traditional therapies.

Further examples of cancers that can be treated using the EPAS1 inhibitor nucleic acids described herein include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidennoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to clear cell renal cell carcinoma, papillary renal cell carcinoma, chromophobe renal cell carcinoma, oncocytoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endothel iosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

In certain embodiments, the present invention provides methods of inhibiting unwanted proliferation of a normal cell (e.g., a non-cancerous and/or non-pathogenic cell). For example, a normal cell may be a cell required for hair growth, and unwanted hair growth may be treated with a method described herein; the unwanted proliferation of a cell can occur in normal hair growth, in trichosis, hypertrichosis, hirsutism, or folliculitis including folliculitis decalvans, folliculitis ulerythematosa reticulata, keloid folliculitis, and pseudofolliculitis. In a further example, a normal cell may be an immune cell that is involved in an undesirable immune response, such as, an autoimmune response, transplant rejection, etc. In an exemplary embodiment, a normal cell may be a normal T cell, and excessive activity or proliferation of T cells is responsible for a number of diseases or conditions including: diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosis, autoimmune thyroiditis, dennatitis (including atopic dennatitis and eczematous dennatitis), psoriasis, Sjogren's Syndrome, Crohn's disease, aphthous ulcer, iritis, conjunctivitis, keratoconjunctivitis, type I diabetes, inflammatory bowel diseases, ulcerative colitis, asthma, allergic asthma, cutaneous lupus erythematosus, sclerodenma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, graft-versus-host disease, cases of transplantation (including transplantation using allogeneic or xenogeneic tissues) such as bone marrow transplantation, liver transplantation, or the transplantation of any organ or tissue, allergies such as atopic allergy, and T-cell neoplasms such as leukemias and/or lymphomas.

In certain embodiments of the methods herein, one or more nucleic acid inhibitors of EPAS1 can be administered together (simultaneously) or at different times (sequentially). For example, two or more dsRNAs, siRNAs, or enzymatic nucleic acids, or combinations thereof, may be used in accordance with the methods described herein.

In certain embodiments, the subject inhibitor nucleic acids of the invention can be used alone. Alternatively, the subject inhibitor nucleic acids may be administered in combination with other conventional anti-cancer agents, anti-pathogen agents, or other therapeutic approaches directed to treatment or prevention of unwanted cell proliferation. For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of a subject nucleic acid agent. When using a combination therapy comprising an EPAS1 inhibitor nucleic acid and another therapeutic agent, such therapeutic agents may be administered separately or conjointly. In certain embodiments, combination therapies may involve an EPAS1 inhibitor nucleic acid and another therapeutic agent that are formulated together or administered as separate formulations.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Certain chemotherapeutic agents may cause unwanted upregulation of EPAS1, thereby inducing the expression of one or more of: cyclin G2, c-Met, CXCR4, IGF2, IGF-BP1, IGF-BP2, IGF-BP3, EGF, WAF-1, TGF-α, TGF-β3, ADM, EPO, IGF2, EG-VEGF, VEGF, NOS2, LEP, LRP1, HK1, HK2, AMF/GP1, ENO1, GLUT1, GAPDH, LDHA, platelet-derived growth factor B, PFKBF3, PKFL, MIC1, NIP3, NIX, RTP801, and/or certain matrix metalloproteinase. By promoting cell survival through its induction of angiogenesis and its activation of anaerobic metabolism, it is believed that the activation of EPAS1 would be counteractive to the other anti-cancer activities of these drugs. Accordingly, EPAS1 inhibitor(s) may be used in combination with certain chemotherapeutic agents for greater efficacy.

Pharmaceutical agents that may be used in the subject combination therapy with EPAS1 inhibitor(s) include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichlioride, topotecan, trastuzumab, tretinoin, vinblastine, vincristine, vindesine, and vinorelbine.

These anti-cancer agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexainethasone, hydrocortisone, methylpednisolone, prednisone, and prenisolone); growth factor signal transduction kinase inhibitors; mitochondrial dysfunction inducers and caspase activators; chromatin disruptors.

These anti-cancer agents may used individually with an EPAS1 inhibitor, or in combination with additional anti-cancer agents. Many combinatorial therapies have been developed in prior art, including but not limited to those listed above. In addition to conventional anti-cancer agents, the agent of the subject method can also be compounds and antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

The methods of the present invention may be advantageous over existing combination therapies by allowing conventional anti-cancer agents to exert greater effect at lower dosage. In preferred embodiments of the present invention, the effective dose ($ED_{50}$) for an anti-cancer agent or combination of anti-cancer agents when used in combination with an EPAS1 inhibitor (e.g., nucleic acid construct) is at least 5-fold less than the $ED_{50}$ for the anti-cancer agent alone (i.e., than the same agent or agents without the EPAS1 inhibitor). Conversely, the therapeutic index (TI) for such anti-cancer agent or combination of such anti-cancer agents when used in combination with an EPAS1 inhibitor (e.g., nucleic acid construct) is at least 5-fold greater than the TI for the anti-cancer agent regimen alone (i.e., than the same agent or agents without the EPAS1 inhibitor).

In certain embodiments, the EPAS1 inhibitor nucleic acids described herein may be administered in combination with other therapeutic agents, including, for example, anti-inflammatory agents, immunosuppressive agents, and/or anti-infective agents (such as for example, antibiotic, antiviral, and/or antifungal compounds, etc.). Exemplary anti-inflammatory drugs include, for example, steroidal (such as, for example, cortisol, aldosterone, prednisone, methylprednisone, triamcinolone, dexamethasone, deoxycorticosterone, and fluorocortisol) and non-steroidal anti-inflammatory drugs (such as, for example, ibuprofen, naproxen, and piroxicam). Exemplary immunosuppressive drugs include, for example, prednisone, azathioprine (Imuran), cyclosporine (Sandimmune, Neoral), rapamycin, antithymocyte globulin, daclizumab, OKT3 and ALG, mycophenolate mofetil (Cellcept) and tacrolimus (Prograf, FK506). Exemplary antibiotics include, for example, sulfa drugs (e.g., sulfanilamide), folic acid analogs (e.g., trimethoprim), beta-lactams (e.g., penacillin, cephalosporins), aminoglycosides (e.g., stretomycin, kanamycin, neomycin, gentamycin), tetracyclines (e.g., chlorotetracycline, oxytetracycline, and doxycycline), macrolides (e.g., erythromycin, azithromycin, and clarithromycin), lincosamides (e.g., clindamycin), streptogramins (e.g., quinupristin and dalfopristin), fluoroquinolones (e.g., ciprofloxacin, levofloxacin, and moxifloxacin), polypeptides (e.g., polymixins), rifampin, mupirocin, cycloserine, aminocyclitol (e.g., spectinomycin), glycopeptides (e.g., vancomycin), and oxazolidinones (e.g., linezolid). Exemplary antiviral agents include, for example, vidarabine, acyclovir, gancyclovir, valganciclovir, nucleoside-analog reverse transcriptase inhibitors (e.g., ZAT, ddI, ddC, D4T, 3TC), non-nucleoside reverse transcriptase inhibitors (e.g., nevirapine, delavirdine), protease inhibitors (e.g., saquinavir, ritonavir, indinavir, nelfinavir), ribavirin, amantadine, rimantadine, relenza, tamiflu, pleconaril, and interferons. Exemplary antifungal drugs include, for example, polyene antifungals (e.g., amphotericin and nystatin), imidazole antifungals (ketoconazole and miconazole), triazole antifungals (e.g., fluconazole and itraconazole), flucytosine, griseofulvin, and terbinafine.

In other aspects, the EPAS1 inhibitor nucleic acids described herein may also be administered in combination with other agents that inhibit HIF1α, such as, for example, the compounds described by Khodadoust and Sharma (US 2006/0135443A1). Such compounds may also be used with the EPAS1 inhibitors described herein, or in further combination with anti-cancer agents described above.

In other embodiments, the present disclosure provides methods of inhibiting angiogenesis and methods of treating angiogenesis-associated diseases. As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

It is understood that methods and compositions of the disclosure are also useful for treating any angiogenesis-independent cancers (tumors). As used herein, the term "angiogenesis-independent cancer" refers to a cancer (tumor) where there is little or no neovascularization in the tumor tissue.

In certain embodiments of such methods, one or more nucleic acid therapeutic agents can be administered, together (simultaneously) or at different times (sequentially). In addition, nucleic acid therapeutic agents can be administered with another type of compounds for treating cancer or for inhibiting angiogenesis.

Depending on the nature of the combinatory therapy, administration of the nucleic acid therapeutic agents of the invention may be continued while the other therapy is being administered and/or thereafter. Administration of the nucleic acid therapeutic agents may be made in a single dose, or in multiple doses. In some instances, administration of the nucleic acid therapeutic agents is commenced at least several days prior to the conventional therapy, while in other instances, administration is begun either immediately before or at the time of the administration of the conventional therapy.

Methods of Administration and Compositions

In certain embodiments, the invention provides compositions comprising one or more EPAS1 inhibitors described herein. In certain embodiments, the compositions are pharmaceutical, suitable for therapeutic uses in a patient. In certain embodiments, the compositions are cosmetic, suitable for cosmetic uses in an animal or a human. In alternative embodiments, the compositions are non-pharmaceutical and non-cosmetic. Generally, the difference between a cosmetic and a pharmaceutical is that the latter requires regulatory approval (e.g., by the Food and Drug Administration) to be used in a human or animal.

Methods for delivering the EPAS1 inhibitors, in particular, the nucleic acids may be based on those methods known in the art (see, e.g., Akhtar et al., *Trends Cell Bio.*, 2:139, 1992; and Delivery Strategies for Antisense Oligonucleotide Therapeutics, ed. Akhtar, 1995; Sullivan et al., PCT Publication No. WO 94/02595). These protocols can be utilized, modified, or improved for the delivery of virtually any nucleic acid. Nucleic acids can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, *Neuroscience,* 76:1153-1158, 1997). Other approaches include the use of various transport and carrier systems, for example through the use of conjugates and biodegradable polymers. In certain embodiments, a subject EPAS1 inhibitor and the vehicle are combined and formulated in the final dosage form before administration. In alternative embodiments, the subject EPAS1 inhibitor and the vehicle are separately formulated such that they will be combined at the time of administration. For example, the subject EPAS1 inhibitor and the vehicle may be stored in separate compartments of a delivery kit or package, and at the time of administration to a desirable site or through a desirable route, the subject EPAS1 inhibitor and the vehicle are mixed for delivery. The separate compartments can be separate vials in a kit, separate cartridges in a medicine delivery pen (see U.S. Pat. No. 5,542,760), separate cannulas or compartments in a syringe, etc.

In certain embodiments, the subject EPAS1 inhibitors are provided as supramolecular complexes that include polymeric microparticles or nanoparticles as delivery vehicles. As used herein, the terms "microparticles" or "nanoparticles" include microspheres or nanospheres (uniform spheres), microcapsules or nanocapsules (having a core and an outer layer of polymer), and particles of irregular shape.

The invention contemplates uses of polymers that are preferably biodegradable within the time period over which release of the EPAS1 inhibitor is desired or relatively soon thereafter, generally in the range of one year, more typically a few months, even more typically a few days to a few weeks. Biodegradation can refer to either a breakup of the microparticle, that is, dissociation of the polymers forming the microparticles/nanoparticles and/or of the polymers themselves. This can occur as a result of change in pH from the carrier in which the particles are administered to the pH at the site of release, as in the case of the diketopiperazines, hydrolysis, as in the case of poly(hydroxy acids), by diffusion of an ion such as calcium out of the microparticle, as in the case of microparticles or nanoparticles formed by ionic bonding of a polymer such as alginate, and by enzymatic action, as in the case of many of the polysaccharides and proteins. In some cases linear release may be most useful, although in others a pulse release or "bulk release" may provide more effective results.

Representative synthetic materials are: diketopiperazines, poly(hydroxy acids) such as poly(lactic acid), poly(glycolic acid) and copolymers thereof, polyanhydrides, polyesters such as polyorthoesters, polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, polyvinyl esters, polyvinyl halides, polyvinylpyrrolidone, polyvinylacetate, and poly vinyl chloride, polystyrene, polysiloxanes, polymers of acrylic and methacrylic acids including poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, and cellulose sulphate sodium salt, poly(butic acid), poly(valeric acid), and poly(lactide-co-caprolactone).

Natural polymers include alginate and other polysaccharides including dextran and cellulose, collagen, albumin and other hydrophilic proteins, zein and other prolamines and hydrophobic proteins, copolymers and mixtures thereof. As used herein, chemical derivatives thereof refer to substitutions, additions of chemical groups, for example, alkyl, alkylene, hydroxylations, oxidations, and other modifications routinely made by those skilled in the art.

Bioadhesive polymers include bioerodible hydrogels described by H. S. Sawhney, C. P. Pathak and J. A. Hubell in *Macromolecules* 26:581-587, 1993 polyhyaluronic acids, casein, gelatin, glutin, polyanhydrides, polyacrylic acid, alginate, chitosan, and polyacrylates.

For a comprehensive review on drug delivery strategies, see Ho et al., *Curr. Opin. Mol. Ther.* 1:336-343, 1999 and Jain, *Drug Delivery Systems: Technologies and Commercial Opportunities, Decision Resources,* 1998 and Groothuis et al., *J. Neuro Virol.* 3:387-400, 1997. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, intrasternal injection and infusion, and intrahepatic arterial administration (including intrahepatic injection and intrahepatic infusion).

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

In certain embodiments, the subject nucleic acids (e.g., RNAi constructs, and enzymatic nucleic acids) of the present invention are formulated with a pharmaceutically-acceptable carrier. Such therapeutic agents can be administered alone or as a component of a pharmaceutical formulation (composition). The agents may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject nucleic acids include those suitable for systemic, local, oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic or anti-infection agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as a oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject nucleic acid therapeutic agent as an active ingredient.

In solid dosage forms for oral administration (capsules, tablets, pills, dragees, powders, granules, and the like), one or more nucleic acid therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Methods and compositions of the invention can be administered topically, either to skin or to mucosal membranes such as those on the cervix and vagina. This offers the greatest opportunity for direct delivery to unwanted cell proliferation localized to skin or mucosal membranes with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject nucleic acids may be mixed under sterile conditions with a pharmaceutically acceptable carrier, and with any preservatives, buffers, or propellants which may be required. The ointments, pastes, creams and gels may contain, in addition to a subject nucleic acid molecule, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject nucleic acid therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Formulations suitable for inhalation are also provided, and such formulations can be used for pulmonary delivery, which can be localized to the pulmonary system or systemic. Examples of pharmaceutical devices for pulmonary delivery include metered dose inhalers (MDIs) and dry powder inhalers (DPIs). Exemplary delivery systems by inhalation which can be adapted for delivery of the subject EPAS1 inhibitor and/or active agent are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the EPAS1 inhibitor and/or active agent are described in U.S. Pat. Nos. 6,294,153; 6,344,194; 6,071,497, U.S. Patent Application Publication No. 2004/0063654, and PCT applications WO02/066078; WO02/053190; WO01/60420; WO00/66206.

Pressurized metered dose inhalers (pMDIs) are the most commonly used inhaler worldwide. The aerosol is created when a valve is opened (usually by pressing down on the propellant canister), allowing liquid propellant to spray out of a canister. Typically, a drug or therapeutic is contained in small particles (usually a few microns in diameter) suspended in the liquid propellant, but in some formulations the drug or therapeutic may be dissolved in the propellant. The propellant evaporates rapidly as the aerosol leaves the device, resulting in small drug or therapeutic particles that are inhaled. Propellants typically used in such pMDIs include but are not limited to hydrofluoroalkanes (HFAs). A surfactant may also be used, for example, to formulate the drug or therapeutic, with pMDIs. Other solvents or excipients may also be employed with pMDIs, such as ethanol, ascorbic acid, sodium metabisulfate, glycerin, chlorobutanol, and cetylpyridinium chloride. Such pMDIs may further include add-on devices such as, for example, spacers, holding chambers and other modifications.

The third type of inhaler is the dry powder inhaler (DPI). In DPIs, the aerosol is usually a powder, contained within the device until it is inhaled. The therapeutic or drug is manufactured in powder form as small powder particles (usually a few millionths of a meter, or micrometers, in diameter). In many DPIs, the drug or therapeutic is mixed with much larger sugar particles (e.g., lactose monohydrate), that are typically 50-100 micrometers in diameter. The increased aerodynamic forces on the lactose/drug agglomerates improve entrainment of the drug particles upon inhalation, in addition to allowing easier filling of small individual powder doses. Upon inhalation, the powder is broken up into its constituent particles with the aid of turbulence and/or mechanical devices such as screens or spinning surfaces on which particle agglomerates impact, releasing the small, individual drug powder particles into the air to be inhaled into the lung. The sugar particles are usually intended to be left behind in the device and/or in the mouth-throat.

One aspect of the invention provides an aerosol composition comprising an EPAS1 inhibitor. An aerosol composition can be a composition comprising aerosolized EPAS1 inhibitor or a composition comprising an EPAS1 inhibitor in a formulation suitable for aerosolization. The EPAS1 inhibitor may be formulated in combination with an additional active agent, and the combination formulation is suitable for aerosolization. Alternatively, the EPAS1 inhibitor and an additional active agent may be formulated separately, such that they will be combined after aerosolization occurs or after being administered to a subject.

Pharmaceutical compositions suitable for parenteral administration may comprise one or more nucleic acid agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more nucleic acid agents in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

Formulations for intravaginal or rectal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In certain embodiments, the nucleic acids of the instant invention are formulated with a pharmaceutically acceptable agent that allows for the effective distribution of the nucleic acids in the physical location most suitable for their desired activity. Non-limiting examples of such pharmaceutically acceptable agents include: PEG, phospholipids, phosphorothioates, P-glycoprotein inhibitors (such as Pluronic P85) which can enhance entry of drugs into various tissues, biodegradable polymers, such as poly (DL-lactide-coglycolide) microspheres for sustained release delivery after implantation (Emerich, D F et al., *Cell Transplant,* 8:47-58, 1999), and loaded nanoparticles such as those made of polybutylcyanoacrylate, which can deliver drugs across the blood brain barrier and can alter neuronal uptake mechanisms (*Prog Neuropsychopharmacol Biol Psychiatry* 23:941-949, 1999).

In other embodiments, certain of the nucleic acids of the instant invention can be expressed within cells from eukaryotic promoters (e.g., Izant and Weintraub, *Science* 229:345, 1985; McGarry and Lindquist, *Proc. Natl. Acad. Sci. USA* 83:399, 1986; Scanlon et al., *Proc. Natl. Acad. Sci. USA* 88:10591-5, 1991; Kashani-Sabetetal., *Antisense Res. Dev.* 2:3-15, 1992; Dropulic et al., *J. Virol.* 66:1432-41, 1992; Weerasinghe et al., *J. Virol.* 65:5531-4, 1991; Ojwang et al., *Proc. Natl. Acad. Sci. USA* 89:10802-6, 1992; Chen et al., *Nucleic Acids Res.* 20:4581-9, 1992; Sarver et al., *Science* 247:1222-1225, 1990; Thompson et al., *Nucleic Acids Res.* 23:2259, 1995; Good et al., *Gene Therapy,* 4:45, 1997). Those skilled in the art realize that any nucleic acid can be expressed in eukaryotic cells from the appropriate DNA/RNA vector. The activity of such nucleic acids can be augmented by their release from the primary transcript by an enzymatic nucleic acid (Draper et al, PCT WO 93/23569, and Sullivan et al., PCT WO 94/02595; Ohkawa et al., *Nucleic Acids Symp. Ser.* 27:15-6, 1992; Taira et al., *Nucleic Acids Res.* 19:5125-30, 1991; Ventura et al., *Nucleic Acids Res.* 21:3249-55, 1993; Chowrira et al., *J. Biol. Chem.* 269:25856, 1994; all of these references are hereby incorporated in their totalities by reference herein). Gene therapy approaches specific to the CNS are described by Blesch et al., *Drug News Perspect.* 13:269-280, 2000; Peterson et al., *Cent. Nerv. Syst. Dis.* 485-508, 2000; Peel and Klein, *J. Neurosci. Methods* 98, 95-104, 2000; Hagihara et al., *Gene Ther.* 7:759-763, 2000; and Herrlinger et al., *Methods Mol. Med.* 35:287-312, 2000. AAV-mediated delivery of nucleic acid to cells of the nervous system is further described by Kaplitt et al., U.S. Pat. No. 6,180,613.

In another aspect of the invention, RNA molecules of the present invention are preferably expressed from transcription units (see for example Couture et al., *TIG* 12:510, 1996)

inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the nucleic acids are delivered as described above, and persist in target cells. Alternatively, viral vectors can be used that provide for transient expression of nucleic acids. Such vectors can be repeatedly administered as necessary. Once expressed, the nucleic acid binds to the target mRNA. Delivery of nucleic acid expressing vectors can be systemic, such as by intravenous or intramuscular administration, by administration to target cells explanted from the patient followed by reintroduction into the patient, or by any other means that would allow for introduction into the desired target cell (for a review see Couture et al., *TIG* 12:510, 1996).

In one aspect, the present invention contemplates an expression vector comprising a nucleic acid sequence encoding at least one of the nucleic acids of the instant invention. The nucleic acid sequence is operably linked in a manner which allows expression of the nucleic acid of the invention. For example, the present invention features an expression vector comprising: a) a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalysts of the instant invention; and wherein said sequence is operably linked to said initiation region and said termination region, in a manner which allows expression and/or delivery of said nucleic acid. The vector can optionally include an open reading frame (ORF) for a protein operably linked on the 5' side or the 3'-side of the sequence encoding the nucleic acid catalyst of the invention; and/or an intron (intervening sequences).

In certain embodiments including double-stranded nucleic acids, the two strands can be expressed separately and then hybridize in a cell. Such separate expression may be through separate expression constructs or through a single expression construct. Alternatively, the two strands can be expressed together, for example, the two strands of a hairpin RNA may be expressed together.

Regardless of the route of administration selected, the EPAS1 inhibitors of the present invention, which may be used in a suitable hydrated form, and/or the pharmaceutical compositions of the present invention, are formulated into pharmaceutically acceptable dosage forms such as described below or by other conventional methods.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular EPAS1 inhibitor of the present invention employed, the route of administration, the time of administration, the rate of excretion of the particular compound being employed, the duration of the treatment, other drugs, compounds and/or materials used in combination with the particular EPAS1 inhibitor employed, the age, sex, weight, condition, general health and prior medical history of the patient being treated, and like factors well known in the medical arts.

A physician or veterinarian can readily determine and prescribe the effective amount of the pharmaceutical composition required. For example, the physician or veterinarian could start doses of the EPAS1 inhibitors of the invention employed in the pharmaceutical composition at levels lower than that required in order to achieve the desired therapeutic effect and gradually increase the dosage until the desired effect is achieved.

In general, a suitable daily dose of an EPAS1 inhibitor of the invention will be that amount of the compound that is the lowest dose effective to produce a therapeutic effect. Such an effective dose will generally depend upon the factors described above. Generally, intravenous, intracerebroventricular, and subcutaneous doses for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

Pharmaceutical formulations of the present invention also include veterinary compositions, e.g., pharmaceutical preparations of the EPAS1 inhibitors suitable for veterinary uses, e.g., for the treatment of livestock or domestic animals, e.g., dogs. The patient receiving this treatment is any animal in need, including primates, in particular humans, and other non-human mammals such as equines, cattle, swine and sheep; and poultry and pets in general.

The EPAS1 inhibitors may also be formulated for non-pharmaceutical uses, for example, for use as disinfectant to remove pathogens from any pathogen-contaminated objects, or for use as a cosmetic to remove unwanted hair growth. A cosmetic composition can be formulated similarly as certain pharmaceutical compositions (e.g., lotion, ointment, film, patch, etc.) described herein.

The EPAS1 inhibitors, such as RNAi constructs, of the invention may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject RNAi constructs can be provided in formulations also including penetration enhancers, carrier compounds and/or transfection agents.

Representative United States patents that teach the preparation of such uptake, distribution and/or absorption assisting formulations which can be adapted for delivery of RNAi constructs, particularly siRNA molecules, include, but are not limited to, U.S. Pat. Nos. 5,108,921; 5,354,844; 5,416,016; 5,459,127; 5,521,291; 51543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The RNAi constructs of the invention also encompass any pharmaceutically-acceptable salts, esters or salts of such esters, or any other compound which, upon administration to an animal including a human, is capable of providing (directly or indirectly) the biologically active metabolite or residue thereof. Accordingly, for example, the disclosure is also drawn to RNAi constructs and pharmaceutically acceptable salts of the siRNAs, pharmaceutically acceptable salts of such RNAi constructs, and other bioequivalents.

Pharmaceutically-acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexyl amine, ethylenediamine, N-methylglucamine, and procaine (see, for example, Berge et al., "Pharmaceutical Salts," *J. of Pharma Sci.* 66:1-19, 1977). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

For siRNAs, examples of pharmaceutically-acceptable salts include, but are not limited to, (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

An exemplary composition comprises an RNAi construct mixed with a delivery system, such as a liposome system, and optionally including an acceptable excipient. In certain embodiments, the composition is formulated for topical administration.

In certain embodiments, the subject nucleic acids are delivered using polymeric vehicles. The polymeric vehicle may form a microparticle with one or more subject nucleic acids. In certain embodiments, particularly where systemic administration is desirable, the nanoparticles may have a size that is about 10 nm, 20 nm, 30 nm, 40 nm, 50 nm, 60 nm, 70 nm, 80 nm, 90 nm, 100 nm, 120 nm, 150 nm, 200 nm or greater in diameter. In certain embodiments, the nanoparticles may have a size that is about 10-120 nm, 10-100 nm, 50-120 nm, 50-100 nm, 10-70 nm, 50-70 nm, or about 50 nm in diameter. In certain embodiments, the nanoparticle comprises cyclodextrin. In particular embodiments, the nanoparticle comprises cyclodextrin copolymers, for example, the linearized cyclodextrin copolymers as described in U.S. Pat. No. 6,509,323 and U.S. Patent Application Publication No. 2002/0151523 and cyclodextrin-based polymers as described in U.S. Patent Application Publication Nos. 2004/0077595, 2004/0109888, and 2004/0087024. In particular embodiments, the cyclodextrin is modified, for example, having a functionalized end group, such as imidazole-containing CDP. In certain embodiments, the nucleic acids are delivered using inclusion complexes such as those described in U.S. Pat. Nos. 7,018,609 and 7,166,302 and U.S. Patent Application Publication No., and 2004/0063654. In certain embodiments, the delivery system or vehicle may further include one or more modifiers or modifying components, for example, a modifier that can change the surface chemistry of a microparticle. The modifier may be an anionic component. The modifier may be a ligand that targets to certain tissue(s) or cell type(s), as described below. The modifier may be a polyethylene glycol (PEG) molecule, for example, a PEG5000 molecule.

In certain embodiments, the EPAS1 inhibitors or pharmaceutical compositions thereof can be associated with one or more ligands effective to bind to specific cell surface proteins or matrix on the target cell, thereby facilitating sequestration of the complex to target cells, and in some instances, enhancing uptake of the RNAi construct by the cell. Merely to illustrate, examples of ligands suitable for use in targeting the supramolecular complexes and liposomes of the present invention to specific cell types are listed in the Table below.

TABLE 7

Suitable ligands for targeted delivery to a variety of cell types.

| Ligand | Receptor | Cell type |
|---|---|---|
| folate | folate receptor | epithelial carcinomas, bone marrow stem cells |
| water soluble vitamins | vitamin receptor | various cells |
| pyridoxyl phosphate | CD4 | CD4 + lymphocytes |
| apolipoproteins | LDL | liver hepatocytes, vascular endothelial cells |
| insulin | insulin receptor | |
| transferrin | transferrin receptor | endothelial cells |
| transferrin | megalin | Kidney proximal tubule cells |
| galactose | asialoglycoprotein receptor | liver hepatocytes |
| sialyl-Lewis$_X$ | E, P selectin | activated endothelial cells |
| Mac-1 | L selectin | neutrophils, leukocytes |
| VEGF | Flk-1, 2 | tumor epithelial cells |
| basic FGF | FGF receptor | tumor epithelial cells |
| EGF | EGF receptor | epithelial cells |
| VCAM-1 | $a_4b_1$ integrin | vascular endothelial cells |
| ICAM-1 | $a_Lb_2$ integrin | vascular endothelial cells |
| PECAM-1/CD31 | $a_vb_3$ integrin | vascular endothelial cells, activated platelets |
| osteopontin | $a_vb_1$ integrin | endothelial cells and |
| | $a_vb_5$ integrin | smooth muscle cells in atherosclerotic plaques |

TABLE 7-continued

Suitable ligands for targeted delivery to a variety of cell types.

| Ligand | Receptor | Cell type |
| --- | --- | --- |
| RGD sequences | $a_vb_3$ integrin | tumor endothelial cells, vascular smooth muscle cells |
| HIV GP 120/41 or GP120 | CD4 | CD4 + lymphocytes |

In certain embodiments, the EPAS1 inhibitors or pharmaceutical compositions thereof can be associated with one or more targeting ligands comprising galactose or transferrin. Megalin, a surface receptor capable of binding transferrin, is overexpressed on clear-cell renal cell carcinoma (RCC) (Schuetz et al., *J Mol Diagn.* 7:206-18,2005). It has also been shown that transferrin receptor is overexpressed during hypoxic conditions (Tacchini et al., *J. Biol. Chem.* 274:24142-6, 1999; Lok and Ponka, *J Biol. Chem.* 274:24147-52, 1999). Clear-cell RCC also highly upregulates transferrin receptor, making transferrin a desirable targeting ligand for treating disorders of the kidney, in particular, renal cancer. Exemplary ligands that comprise galactose include, for example, lactose and similar molecules. The hepatic asialoglycoprotein receptor (ASGPR) is a C-type lectin that is expressed on the surface of hepatocytes. ASGPR binds glycoproteins with terminal β-D-galactose (Gal) or N-acetylgalactosamine (GalNAc). The affinity of ligands for the ASGPR is dependent on type (Gal vs. GalNAc), number (tetraantennary>triantennary>>biantennary>>monantennary) and arrangement of multiantennary residues. Each polypeptide subunit of the ASGPR (human is a tetramer) can bind a single terminal Gal or GalNAc.

Other Embodiments

Renal Cancer

Renal cell carcinoma (RCC), the most common form of kidney cancer, affects about 3 in 10,000 people. This growing incidence results in about 38,000 new cases in the U.S. yearly. Despite three new drugs being approved for RCC in recent years, responses are mostly partial and of limited duration (Costa and Drabkin, *Oncologist* December; 12(12):1404-15, 2007). Here, we propose a new therapeutic agent for the treatment of renal cancer. Inhibition of EPAS1 by non-virally delivered short interfering RNAs (siRNAs) provides an efficacious therapy for renal cancer. The inhibition of EPAS1 alone and/or in combination with low dose chemotherapeutic agents results in a therapeutic mechanism of action for renal cancer with an anticipated superior safety profile to current therapies.

Seventy-five percent of cases of RCC are clear-cell carcinomas, and a majority are driven by dysfunction of the von Hippel-Lindau (VHL) gene. VHL loss of function and other non-VHL pathways leading to RCC share aberrant activation of the hypoxic response, such as upregulation of vascular endothelial growth factor (VEGF) and consequent neoangiogenesis. The VHL gene product, pVHL, is part of a complex that recognizes the α subunit of the transcription factor hypoxia-induced factor (HIF) and targets it for polyubiquitination and proteasomal degradation. Therefore, VHL-deficient cancer cells have increased levels of HIF, making them good candidates for treatment that reduces cellular HIF levels. Indeed, it has been shown that inhibition of EPAS1 (one of three human HIFα proteins), via retrovirally-mediated delivery of shRNAs targeting EPAS1, is sufficient to suppress the growth of pVHL-defective tumors in animals (Kondo et al., *PLOS Biology* 1(3): 439-444, 2003).

The action of the von Hippel-Lindau (VHL) tumor suppressor gene product is implicated in hypoxic gene regulation, in both normal and diseased cells. Individuals with VHL disease are predisposed to renal cysts, clear cell renal carcinoma, phaeochromocytoma, haemangioblastomas of the central nervous system, angiomas of the retina, islet cell tumors of the pancreas, and endolymphatic sac tumors (Pugh and Ratcliffe, *Semin. Cancer. Biol.* 2003, 13:83-89, 2003). The VHL gene product participates in ubiquitin-mediated proteolysis by acting as the recognition component of the E3-ubiquitin ligase complex involved in the degradation of hypoxia-inducible factor alpha subunits (Cockman et al., *J. Biol. Chem.* 275:25733-25741, 2000; Ohh et al., *Nat. Cell Biol.* 2:423-427, 2000). In normal cells, VHL/HIF complexes form and target HIF alpha subunits for destruction (Maxwell et al., *Nature* 399:271-275, 1999). This is proposed to occur through hydroxylation of the oxygen-dependent domain of EPAS1 and subsequent recognition by the VHL gene product, as recognition of a homologous oxygen-dependent domain is the mechanism by which the VHL protein recognizes HIF1α (Maxwell et al., *Nature* 399:271-275, 1999). EPAS1 is in fact hydroxylated by the enzyme prolyl 4-hydroxylases in vitro (Hirsila et al., *J. Biol. Chem.* 2003).

EPAS1 Inhibition for Renal Cancer

EPAS1 mRNA is primarily expressed in highly vascularized adult tissues, such as lung, heart and liver, and in the placenta and endothelial cells of the embryonic and adult mouse (Hogenesch et al., *J. Biol. Chem.* 272:8581-8593, 1997). Comparison of normal human tissues and cancers reveals that EPAS1 protein is not detectable in normal tissue, but is easily visualized in malignant tissues (Talks et al., *Am. J. Pathol.* 157:411-421, 2000). The requirement for expression of EPAS1 in development is demonstrated by the abnormalities observed in EPAS1 gene deficient mouse embryos, which include the disruption of catecholamine homeostasis and lack of protection against heart failure observed (Tian et al., *Genes Dev.* 12:3320-3324, 1998).

EPAS1 expression and HIF transcriptional activity are precisely regulated by cellular oxygen concentration. Whereas changes in oxygen levels do not affect HIF1-beta protein levels, the abundance of the alpha subunits is markedly increased upon exposure of cells to hypoxia, primarily due to stabilization of the alpha subunit protein (Safran and Kaelin, *J. Clin. Invest.* 111:779-783, 2003). EPAS1 mRNA and protein is expressed at low levels in tissue culture cells, but protein expression is markedly induced by exposure to 1% oxygen, a hypoxic state (Wiesener et al., *Blood* 92:2260-2268, 1998). The hypoxia-inducible factor 2 alpha/hypoxia-inducible factor 1 beta heterodimer protein binds to the hypoxic response element, which contains the core recognition sequence 5'-TACGTG-3' and is found in the cis-regulatory regions of hypoxia-regulated genes (Ema et al., *Proc. Natl. Acad. Sci. U.S.A.* 94:4273-4278, 1997; Hogenesch et al., *J. Biol. Chem.* 272:8581-8593, 1997). Binding of the heterodimer to the HRE induces gene expression. Upon return to normoxic conditions, EPAS1 protein is rapidly degraded (Wiesener et al., *Blood* 92:2260-2268, 1998).

The mitogen-activated protein kinase (MAPK) pathway is critical for EPAS1 activation. Inhibition of a dual specificity protein kinase that directly phosphorylates MAPK prevents EPAS1 trans-activation during hypoxia (Conrad 1999; Conrad, 2001). However, the inhibitor does not prevent EPAS1 phosphorylation, thus, while the MAPK pathway regulates the activity of EPAS1, it does not directly phosphorylate the protein (Conrad et al., *Comp. Biochem. Physiol. B. Biochem. Mol. Biol.* 128:187-204, 2001; Conrad et al., *J. Biol. Chem.* 274:33709-33713, 1999). The Src family kinase pathway is also implicated in regulation of EPAS1. A specific inhibitor of the Src family of kinases abolishes the hypoxia-induced expression of EPAS1 mRNA in human lung adenocarcinoma cells (Sato et al., *Am. J. Respir. Cell Mol. Biol.* 26:127-134, 2002).

The maintenance of oxygen homeostasis, in addition to being required in physiological development, is also required in tumor growth. Tumor cells experience hypoxia because blood circulates poorly through the aberrant blood vessel that tumors establish. Although hypoxia is toxic to cancer cells, they survive as a result of genetic and adaptive changes that allow them to thrive in a hypoxic environment. One such adaptation is an increase in the expression of the angiogenic growth factor named vascular endothelial growth factor (VEGF). VEGF is a key angiogenic factor secreted by cancer cells, as well as normal cells, in response to hypoxia (Harris, *Nat. Rev. Cancer* 2:38-47, 2002; Maxwell et al., *Curr. Opin. Genet. Dev.* 11:293-299, 2001).

Hemangioblastomas, the most frequent manifestation of VHL gene mutations, exhibit overexpression of VEGF mRNA in their associated stromal cells. The VEGF mRNA overexpression is highly correlated with elevated expression of EPAS1 mRNA. This finding suggests a relationship between loss of function of the VHL gene, and transcriptional activation of the VEGF gene, possibly through EPAS1 activity in VEGF-dependent vascular growth (Flamme et al., *Am. J. Pathol.* 153:25-29, 1998).

The tumor suppressive activity of the VHL gene product can be overridden by the activation of HIF target genes in human renal carcinoma cells in vivo. VHL gene product mutants lose the ability to target HIF for ubiquitin-mediated destruction, suggesting that down regulation of HIF and VHL tumor suppressor function are intimately linked (Kondo et al., *Cancer Cell* 1:237-246, 2002). In contrast to human renal cell carcinoma, the product of the tuberous sclerosis complex-2 (Tsc-2) gene product, rather than VHL gene, is the primary target for rodent renal cell carcinoma (Liu et al., *Cancer Res.* 63:2675-2680, 2003). Rat RCC cells lacking Tsc-2 function exhibit stabilization of EPAS1 protein and upregulation of VEGF, and were highly vascularized (Liu et al., *Cancer Res.* 63:2675-2680, 2003).

A link between elevated EPAS1 activity and angiogenesis has also been demonstrated by experiments that show how HIF activity regulates VEGF expression. Normal human kidney cells typically have low levels of EPAS1, but upon introduction of a vector encoding EPAS1 into these cells, VEGF mRNA and protein levels increase significantly (Xia et al., *Cancer* 91:1429-1436, 2001). When EPAS1 was inhibited, VEGF expression was significantly decreased, thus demonstrating a direct link between EPAS1 activity and VEGF expression (Xia et al., *Cancer* 91:1429-1436, 2001). Similarly, a dose-dependent increase in VEGF mRNA is observed when human umbilical vein cells are transduced with a virus encoding EPAS1 (Maemura et al., *J. Biol. Chem.* 274:31565-31570, 1999). Expression of a mutated EPAS1 that lacks a transactivation domain inhibits the induction of VEGF mRNA during hypoxia, a finding that further suggests that EPAS1 is an important regulator of VEGF expression (Maemura et al., *J. Biol. Chem.* 274:3 1565-3 1570, 1999).

A correlation between HIF activity and VEGF expression is also observed in malignant cells and tissues. EPAS1 can be readily detected in renal cell carcinoma (RCC) cell lines in the absence of a vector encoding EPAS1 (Xia et al., *Cancer* 91:1429-1436, 2001). Significant increases in EPAS1 and VEGF mRNA in renal cell carcinoma tissue samples, compared to normal tissue, suggest that abnormal activation of EPAS1 may be involved in the angiogenesis of RCC (Xia et al., *Cancer* 91:1429-1436, 2001).

Taken together, these studies demonstrate that elevated EPAS1 confers aggressive tumor behavior, and that targeting the HIF pathway may aid the treatment of several different types of cancers. In particular, these studies and others not reported here show that EPAS1 is an excellent target for renal cancer. The compositions described herein may be delivered using renal cell-targeting particles that that deliver siRNAs against EPAS1 to diseased renal tissue in order to inhibit the expression of EPAS1 to treat renal cell carcinoma. In certain embodiments, the delivery technology RONDEL™ may be used as a suitable vehicle for renal-specific delivery of inhibitor nucleic acid described herein. RONDEL™ technology involves the use of cyclodextrin-containing polymers that form the foundation for its two-part siRNA delivery system. The first component is a linear, cyclodextrin-containing polycation that, when mixed with small interfering RNA, binds to the anionic "backbone" of the siRNA. The polymer and siRNA self-assemble into nanoparticles smaller than 100 nm in diameter that fully protect the siRNA from nuclease degradation in serum. The siRNA delivery system has been designed to allow for various delivery routes, including intravenous injection. Upon delivery to a target cell, a targeting ligand binds to membrane receptors on the cell surface and the RNA-containing nanoparticle is taken into the cell by endocytosis and released from the delivery vehicle.

A renal therapeutic agent of the invention can be a small molecule, a peptide or a peptide analog, such as for example, a peptidomimetic, and a nucleic acid. A nucleic acid renal therapeutic agent of the invention can be an antisense RNA, an RNAi construct (e.g., an siRNA), or a ribozyme. A nucleic acid renal therapeutic agent may also be a gene therapy construct, such as for example, an expression construct that delivers a gene to be expressed in renal cells.

A renal therapeutic agent of the present invention is effective against a renal disease or condition, e.g., caused by unwanted proliferation of cells. Methods and compositions of the inventions may be useful or effective against any renal disease or condition, including, but not limited to, renal cancer (e.g., clear cell renal cell carcinoma, papillary renal cell carcinoma, chromophobe renal cell carcinoma, and oncocytoma), acute renal failure, chronic renal failure, glomerular nephritis, diabetic nephropathy, and the like. Accordingly, a pharmaceutical composition of the invention can be effective against one or more renal diseases or conditions, such as those described herein.

In certain embodiments, a renal therapeutic agent targets a gene that is dysregulated in renal cells of a patient with a renal disease or condition. The gene may be a specific to renal cells. Alternatively, the gene is not a renal-specific gene, such as for example, a gene with similar or lower level of expression in renal cells as compared to other cells and tissues, and the expression and/or activity of that gene is altered in renal cells of a patient with a renal disease or condition as compared to renal cells from a normal kidney. For example, EPAS1 is dysregulated in renal cell carcinoma. That is, EPAS1 may be overexpressed in renal cell carcinoma cells with abnormal activity of the von Hippel-Lindau (VHL) protein, but is expressed at undetectable levels in normal renal cells. A renal therapeutic agent targeting EPAS1 may be a nucleic acid agent that specifically reduces or inhibits expression of EPAS1, and such a nucleic acid agent can be an antisense molecule, an RNAi construct (e.g., an siRNA construct), or a ribozyme.

Another aspect of the invention provides methods for treating a patient having a renal disease or condition. The method generally comprises systemically administering to the patient a therapeutically effective amount of a pharmaceutical composition of the invention. System administration can be achieved via various routes of delivery, such as for example, i.v. or i.p. injection, transdermal delivery, pulmonary delivery, or oral uptake.

In certain aspects, the invention provides methods for treating a patient suffering from a cancer, comprising: (a) identifying in the patient a tumor having a plurality of cancer cells that express EPAS1 (or express EPAS1 at a level above a predetermined threshold); and (b) administering to the patient, as appropriate, a subject nucleic acid targeting EPAS1. A method may include, as a diagnostic part, identifying in the patient a tumor having a plurality of cancer cells having a gene amplification of EPAS1. Gene amplifications may be detected in a variety of ways, including, for example, fluorescent in situ hybridization (FISH) or representational oligonucleotide microarray analysis (ROMA).

In certain embodiments, the invention provides methods for treating a patient suffering from a renal disease such as clear-cell RCC by administering an EPAS1 inhibitor(s) as part of a delivery vehicle as described herein. In other embodiments, the treatment method includes profiling patients prior to therapy so as to determine their VHL status. That is, patients with appropriate VHL status may be selected as desirable candidates for the present method. Appropriate VHL status may be determined through a variety of art recognized methods. For example, Hui et al. (U.S. Pat. No. 6,013,436) disclose kits and methods for diagnosing mutations in VHL that may be, for example, insertion or deletion mutations. Additionally, Boman (US 2007/031881 A1) teaches immunoassays for detecting cellular levels of VHL to distinguish between cells that are homozygous and those that are heterozygous for a wild-type allele. Furthermore, Henderson (US 2004/166491 A1) teaches methods of diagnosing single nucleotide polymorphisms (SNP) in the VHL gene. When located in a coding region, the presence of the SNP can result in the production of a protein that is non-functional or has decreased function. More frequently, SNPs occur in noncoding regions. If the SNP occurs in a regulatory region, it may affect expression of the VHL protein. For example, the presence of a SNP in a promoter region, may cause decreased expression of a protein. As such, the present method may include, as a diagnostic part, identifying in the patient a tumor having a deficient variant of VHL.

The invention contemplates a variety of renal therapeutic agents, including, but not limited to, small molecule agents, peptides or peptide analogs (including peptidomimetics), nucleic acid agents (such as for example, RNAi constructs including siRNA constructs, antisense molecules, enzymatic nucleic acids, or other gene therapy constructs), vaccines, or medications currently available or under development (e.g., in clinical trials). Such renal therapeutic agents may be delivered according to the methods described by Davis et al. (US 2006/0263435 A1).

EXEMPLIFICATION

The disclosure now being generally described, will be more readily understood by reference to the following examples, which are included merely for purposes of illustration of certain aspects and embodiments of the present disclosure, and are not intended to limit the disclosure.

Example 1

Down Regulation of EPAS1 Expression Using siRNAs

We have now designed and tested a number of siRNAs specific for the EPAS1 sequence for their ability to down regulate expression of EPAS1 both in vitro and in vivo. The sequences for the specific siRNAs are provided herein as SEQ ID NOs: 5-82 (shown in Tables 2-6 above).

As shown in FIG. 2, siRNAs directed against EPAS1 were able to down-regulate EPAS1 expression in A498 (human kidney carcinoma) cells. Each of the three siRNA duplexes against EPAS1 (siEPAS1A, siEPAS1B, and siEPAS1C shown in Table 2 as SEQ ID NOs: 5-10) achieve a reduction of the EPAS1 protein level in A498 cells. In contrast, the siCON1 (a non-targeting control siRNA shown as SEQ ID NOs: 83 and 84 in Table 8 below) shows no apparent down-regulation.

To conduct the experiments shown in FIG. 2, A498 cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Lipofectamine™ RNAiMAX (Invitrogen) and each of the following nucleic acids according to the manufacturer's recommendations:

"siCONTROL" or "siCON1": Non-targeting negative control siRNA;

"siEPAS1A": siRNA spanning the "A" target site of hEPAS1 shown as SEQ ID NOs: 5 and 6 in Table 2 above;

"siEPAS1B": siRNA spanning the "B" target site of hEPAS1 shown as SEQ ID NOs: 7 and 8 in Table 2 above;

"siEPAS1C": siRNA spanning the "C" target site of hEPAS1 shown as SEQ ID NOs: 9 and 10 in Table 2 above.

The nucleic acid complexes were exposed to cells at a final nucleic acid concentration of 10 nM for 4 h, after which the complexes were removed by aspiration and replaced with complete medium. Two days (48 h) post-transfection, total RNA was isolated from all cells by Trizol and reverse-transcribed to cDNA. Relative EPAS1 mRNA levels (with respect to untransfected A498 cells) were determined via qRT-PCR; data was normalized to a housekeeping gene (GAPDH).

TABLE 8

Sequences of control nucleic acids used in the Examples described herein.

| Description | Sequence | Strand | SEQ ID NO |
|---|---|---|---|
| siCONTROL (or siCON1) | 5' uagcgacuaaacacaucaauu 3' | Sense | SEQ ID NO: 83 |
| | 3' uuaucgcugauuuguguaguu 5' | Antisense | SEQ ID NO: 84 |

Example 2

Tiling Experiments for Identification of EPAS1 siRNAs at Each Target Site

Figure 3:
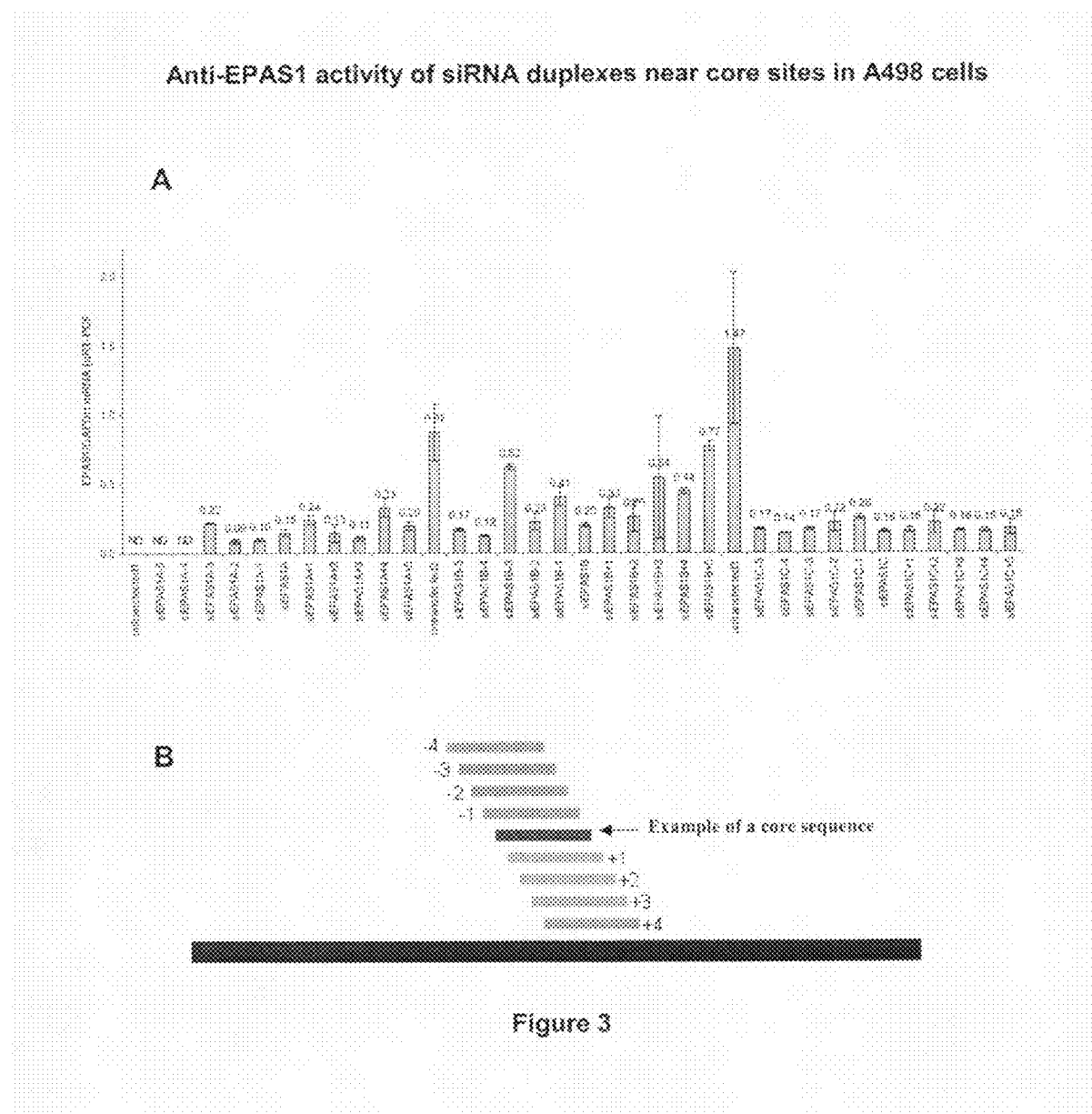
FIG. 3A shows anti-EPAS1 activity of additional siRNA duplexes near initial three sites in A498 cells. Of the duplexes examined, siEPAS1A-2, siEPAS1A-1, siEPAS1A, siEPAS1A+3, siEPAS1B-4, and siEPAS1C-4 showed the most potent anti-EPAS1 activity.
FIG. 3B is an illustration of the design of the tiling experiments.

As shown in FIG. 3A, tiling experiments were used to identify siRNAs directed against EPAS1 having increased potency. To conduct the experiment shown in FIG. 3, A498 (human kidney carcinoma) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Lipofectamine™ RNAiMAX (Invitrogen) and each of the following nucleic acids according to the manufacturer's recommendations:

"siEPAS1A": siRNA duplexes spanning the "A" site of hEPAS1 shown as SEQ ID NOs: 5, 6, and 23-42 in Tables 2 and 4 above:
- siEPAS1A−5: siRNA five nucleotides up-stream of the original "A" site of hEPAS1 shown as SEQ ID NOs: 23 and 24 in Table 4 above;
- siEPAS1A−4: siRNA four nucleotides up-stream of the original "A" site of hEPAS1 shown as SEQ ID NOs: 25 and 26 in Table 4 above;
- siEPAS1A−3: siRNA three nucleotides up-stream of the original "A" site of hEPAS1 shown as SEQ ID NOs: 27 and 28 in Table 4 above;
- siEPAS1A−2: siRNA two nucleotides up-stream of the original "A" site of hEPAS1 shown as SEQ ID NOs: 29 and 30 in Table 4 above;
- siEPAS1A−1: siRNA one nucleotide up-stream of the original "A" site of hEPAS1 shown as SEQ ID NOs: 31 and 32 in Table 4 above;
- siEPAS1A: siRNA centered around the original "A" site of hEPAS1 shown as SEQ ID NOs: 5 and 6 in Table 2 above;
- siEPAS1A+1: siRNA one nucleotide down-stream of the original "A" site of hEPAS1 shown as SEQ ID NOs: 33 and 34 in Table 4 above;
- siEPAS1A+2: siRNA two nucleotides down-stream of the original "A" site of hEPAS1 shown as SEQ ID NOs: 35 and 36 in Table 4 above;
- siEPAS1A+3: siRNA three nucleotides down-stream of the original "A" site of hEPAS1 shown as SEQ ID NOs: 37 and 38 in Table 4 above;
- siEPAS1A+4: siRNA four nucleotides down-stream of the original "A" site of hEPAS1 shown as SEQ ID NOs: 39 and 40 in Table 4 above;
- siEPAS1A+5: siRNA five nucleotides down-stream of the original "A" site of hEPAS1 shown as SEQ ID NOs: 41 and 42 in Table 4 above;

"siEPAS1B": siRNA duplexes spanning the "B" site of hEPAS1 shown as SEQ ID NOs: 7, 8, and 43-62 in Tables 2 and 5 above:
- siEPAS1B−5: siRNA five nucleotides up-stream of the original "B" site of hEPAS1 shown as SEQ ID NOs: 43 and 44 in Table 5 above;
- siEPAS1B−4: siRNA four nucleotides up-stream of the original "B" site of hEPAS1 shown as SEQ ID NOs: 45 and 46 in Table 5 above;
- siEPAS1B−3: siRNA three nucleotides up-stream of the original "B" site of hEPAS1 shown as SEQ ID NOs: 47 and 48 in Table 5 above;
- siEPAS1B−2: siRNA two nucleotides up-stream of the original "B" site of hEPAS1 shown as SEQ ID NOs: 49 and 50 in Table 5 above;
- siEPAS1B−1: siRNA one nucleotide up-stream of the original "B" site of hEPAS1 shown as SEQ ID NOs: 51 and 52 in Table 5 above;
- siEPAS1B: siRNA centered around the original "B" site of hEPAS1 shown as SEQ ID NOs: 7 and 8 in Table 2 above;
- siEPAS1B+1: siRNA one nucleotide down-stream of the original "B" site of hEPAS1 shown as SEQ ID NOs: 53 and 54 in Table 5 above;
- siEPAS1B+2: siRNA two nucleotides down-stream of the original "B" site of hEPAS1 shown as SEQ ID NOs: 55 and 56 in Table 5 above;
- siEPAS1B+3: siRNA three nucleotides down-stream of the original "B" site of hEPAS1 shown as SEQ ID NOs: 57 and 58 in Table 5 above;
- siEPAS1B+4: siRNA four nucleotides down-stream of the original "B" site of hEPAS1 shown as SEQ ID NOs: 59 and 60 in Table 5 above;
- siEPAS1B+5: siRNA five nucleotides down-stream of the original "B" site of hEPAS1 shown as SEQ ID NOs: 61 and 62 in Table 5 above;

"siEPAS1C": siRNA duplexes spanning the "C" site of hEPAS1 shown as SEQ ID NOs: 9, 10, and 63-82 in Tables 2 and 6 above:
- siEPAS1C−5: siRNA five nucleotides up-stream of the original "C" site of hEPAS1 shown as SEQ ID NOs: 63 and 64 in Table 6 above;
- siEPAS1C−4: siRNA four nucleotides up-stream of the original "C" site of hEPAS1 shown as SEQ ID NOs: 65 and 66 in Table 6 above;
- siEPAS1C−3: siRNA three nucleotides up-stream of the original "C" site of hEPAS1 shown as SEQ ID NOs: 67 and 68 in Table 6 above;
- siEPAS1C−2: siRNA two nucleotides up-stream of the original "C" site of hEPAS1 shown as SEQ ID NOs: 69 and 70 in Table 6 above;
- siEPAS1C−1: siRNA one nucleotide up-stream of the original "C" site of hEPAS1 shown as SEQ ID NOs: 71 and 72 in Table 6 above;
- siEPAS1C: siRNA centered around the original "C" site of hEPAS1 shown as SEQ ID NOs: 9 and 10 in Table 2 above;
- siEPAS1C+1: siRNA one nucleotide down-stream of the original "C" site of hEPAS1 shown as SEQ ID NOs: 73 and 74 in Table 6 above;

siEPAS1C+2: siRNA two nucleotides down-stream of the original "C" site of hEPAS1 shown as SEQ ID NOs: 75 and 76 in Table 6 above;

siEPAS1C+3: siRNA three nucleotides down-stream of the original "C" site of hEPAS1 shown as SEQ ID NOs: 77 and 78 in Table 6 above;

siEPAS1C+4: siRNA four nucleotides down-stream of the original "C" site of hEPAS1 shown as SEQ ID NOs: 79 and 80 in Table 6 above;

siEPAS1C+5: siRNA five nucleotides down-stream of the original "C" site of hEPAS1 shown as SEQ ID NOs: 81 and 82 in Table 6 above.

See FIG. 3B for illustration of the experimental design of the tiling experiments.

These complexes were exposed to cells at a final nucleic concentration of 10 nM for 4 h, after which they were removed by aspiration and replaced with complete medium. Two days (48 h) post-transfection, total RNA was isolated from all cells by Trizol and reverse-transcribed to cDNA. Relative EPAS1 mRNA levels (with respect to untransfected A498 cells) were determined via qRT-PCR; data were normalized to GAPDH.

Of the duplexes examined here, the following six duplexes showed the most potent anti-EPAS1 activity: siEPAS1A−2, siEPAS1A−1, siEPAS1A, siEPAS1A+3, siEPAS1B−4, and siEPAS1C−4. These duplexes were further examined below.

Example 3 siRNA Against EPAS1 Reduces Growth Potential of Cultured A498 Cells

Figure 4:
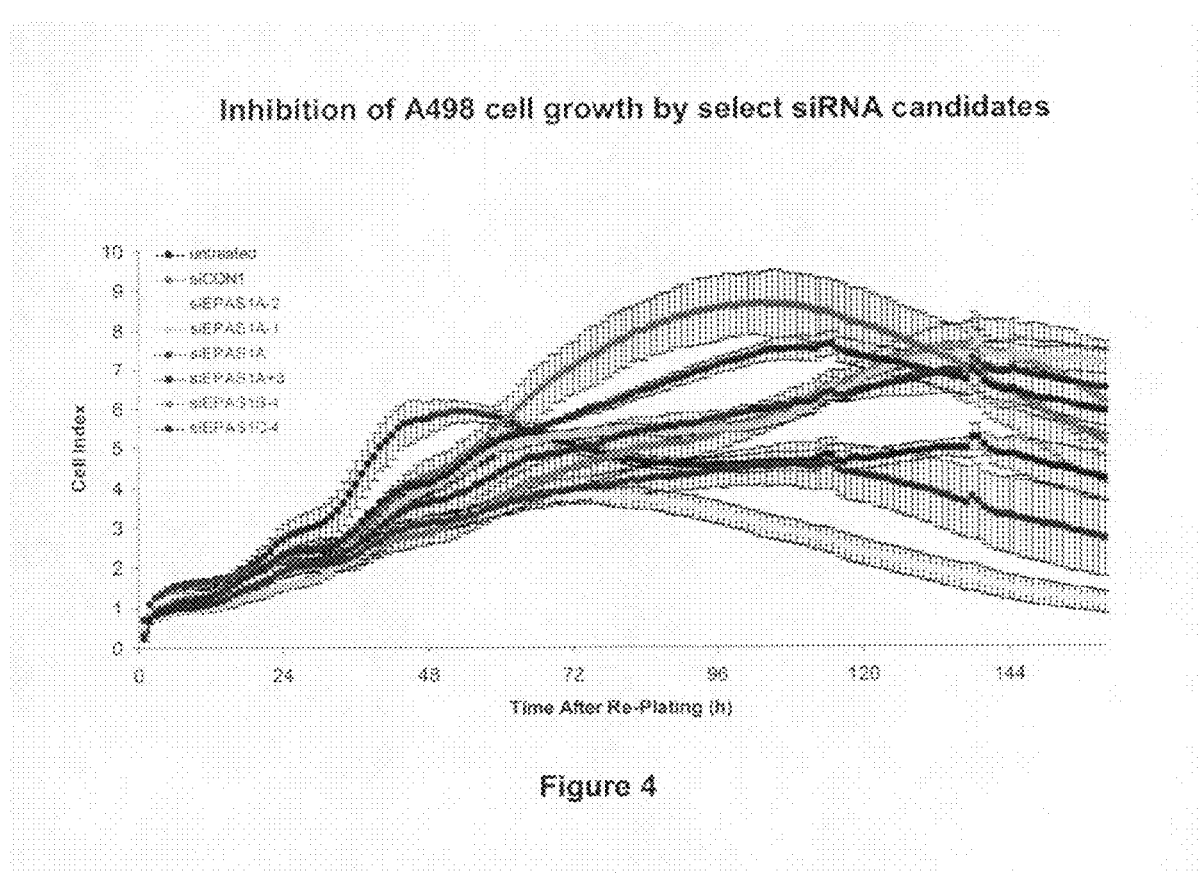
FIG. 4 further examines the effects of several anti-EPAS1 siRNA duplexes (those which showed the most potent anti-EPAS1 activity; see FIG. 3A) on A498 cell growth. Of the siRNA duplexes tested, siEPAS1A-2 and siEPAS1A are the most significant inhibitors of A498 cell growth as measured by real-time cell electronic sensing (RT-CES).

As shown in FIG. 4, siEPAS1A−2, siEPAS1A−1, siEPAS1A, siEPAS1A+3, siEPAS1B−4, and siEPAS1C−4 siRNA duplexes were examined for their ability to reduce growth potential of cultured human A498 cells. siCON1 was used as a non-targeting control. siEPAS1A−2 and siEPAS1A elicited the most significant inhibitions in A498 cell growth (RT-CES).

To conduct the experiments shown in FIG. 4, A498 (human kidney carcinoma) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Lipofectamine™ RNAiMAX (Invitrogen) and the nucleic acids according to the manufacturer's recommendations.

Example 4 siEPAS1A−2 Reduces Cellular EPAS1 mRNA Levels

Figure 5:
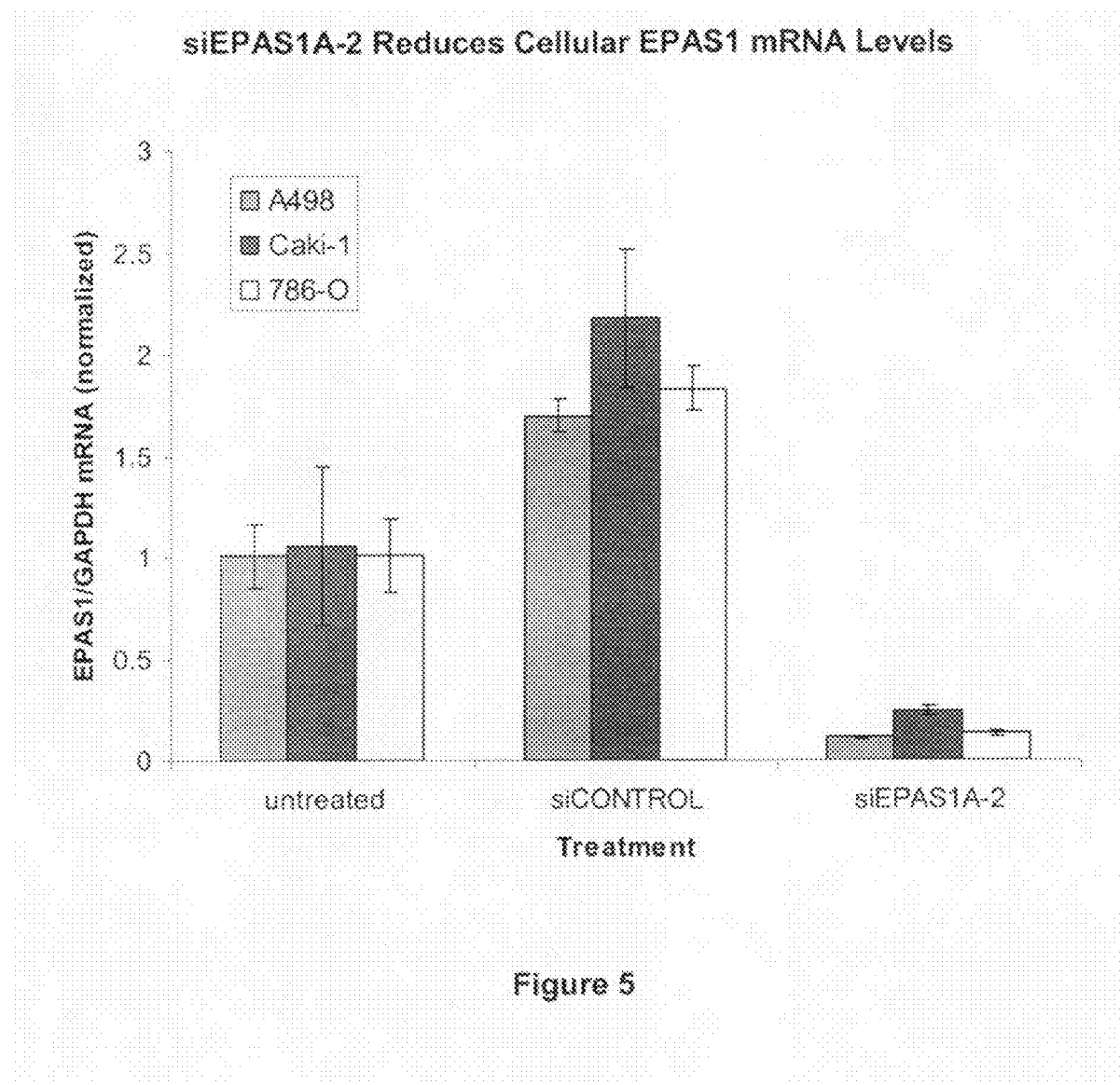
FIG. 5 demonstrates that siEPAS1A-2 (SEQ ID NOs: 29 and 30) effectively reduces cellular EPAS1 mRNA levels in cultured human renal cell carcinoma cell lines (A-498, 786-O, and Caki-1).

The level of EPAS1 mRNA in cultured human renal cell carcinoma (A-498, 786-O, and Caki-1) cells was examined by qRT-PCR after transfection of cells with siEPAS1A−2 (sequence pair SEQ ID NO: 29 and 30). Very strong sequence-specific reduction of EPAS1 mRNA levels was seen in all three cell lines. (See FIG. 5; error bars represent the standard deviation of three replicate measurements.)

Each cell line was transfected either with siEPAS1A−2 or a non-targeting control siRNA duplex (siCONTROL) using a commercially-available transfection reagent (Lipofectamine™ RNAiMAX; Invitrogen), at an siRNA concentration of 20 nM, and an exposure time of 4 h. Forty-eight (48) hours post-transfection, cellular RNA was isolated and reverse-transcribed, and the levels of EPAS1 mRNA (normalized to GAPDH) were measured in A498, Caki-1, and 786-O cells that were untransfected, transfected with siEPAS1A−2, or transfected with a non-targeting control siRNA (siCONTROL).

Example 5 siEPAS1A−2 Reduces Cellular Proliferation Rate

In order to be an effective anti-cancer agent, siEPAS1A−2 should not only reduce cellular EPAS1 levels but also achieve cellular growth inhibition. An anti-proliferative effect upon EPAS1 knockdown is expected in those cells that are von Hippel-Lindau null ($VHL^{-/-}$). 786-O and A-498 human RCC cells lack wild-type pVHL, whereas Caki-1 cells are $VHL^{+/+}$.

Figure 6A:
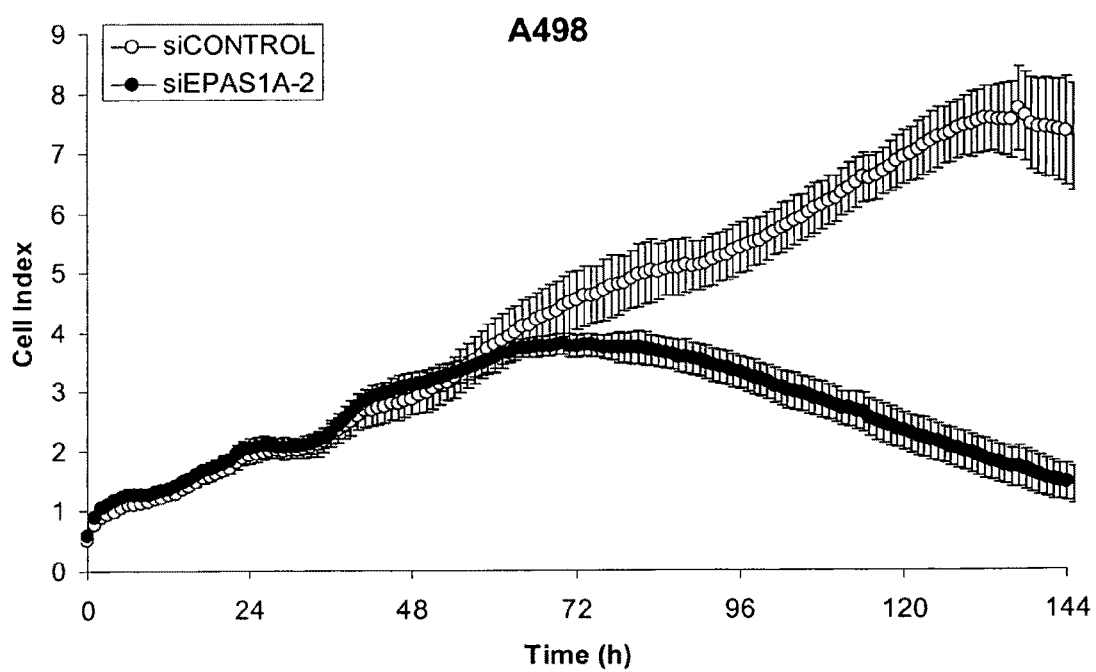
FIGS. 6A-6C shows reduction in the rate of cellular proliferation upon treatment with siEPAS1A-2. As expected based upon VHL status, siEPAS1A-2 achieved a significant anti-proliferative effect in A498 and 786-O cells, but not in Caki-1 cells, indicating that cancer cells deficient in VHL are good candidates for treatment that reduces cellular HIF levels.
Figure 6B:
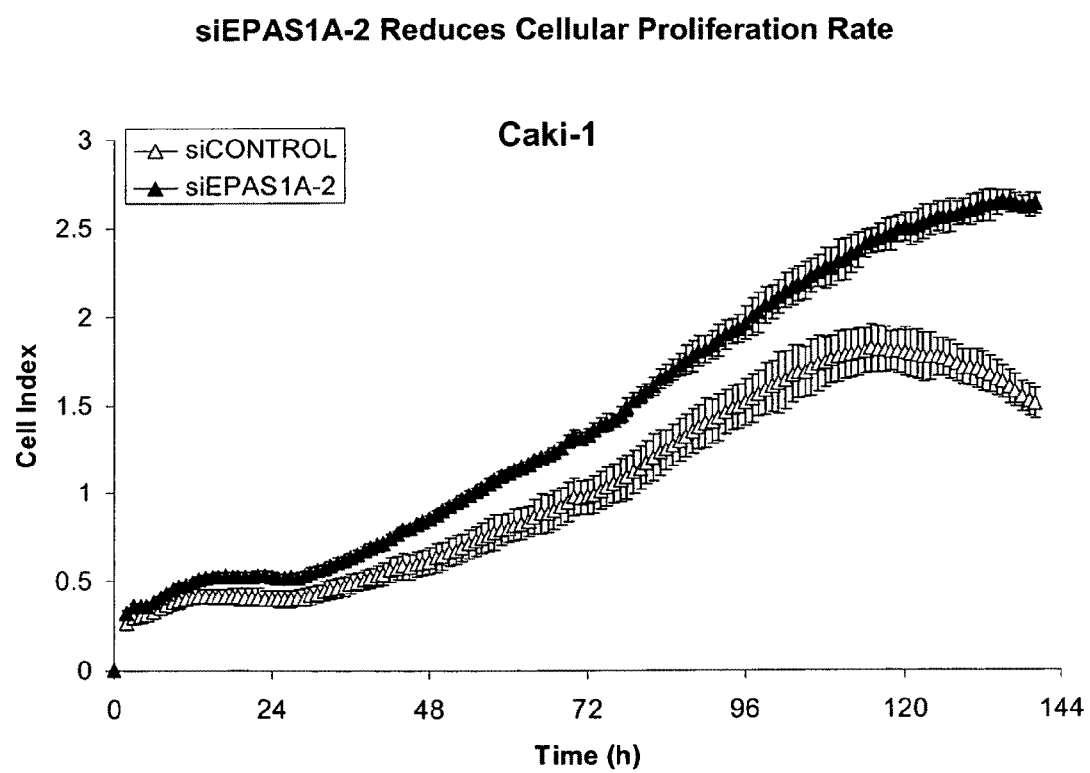
Figure 6C:
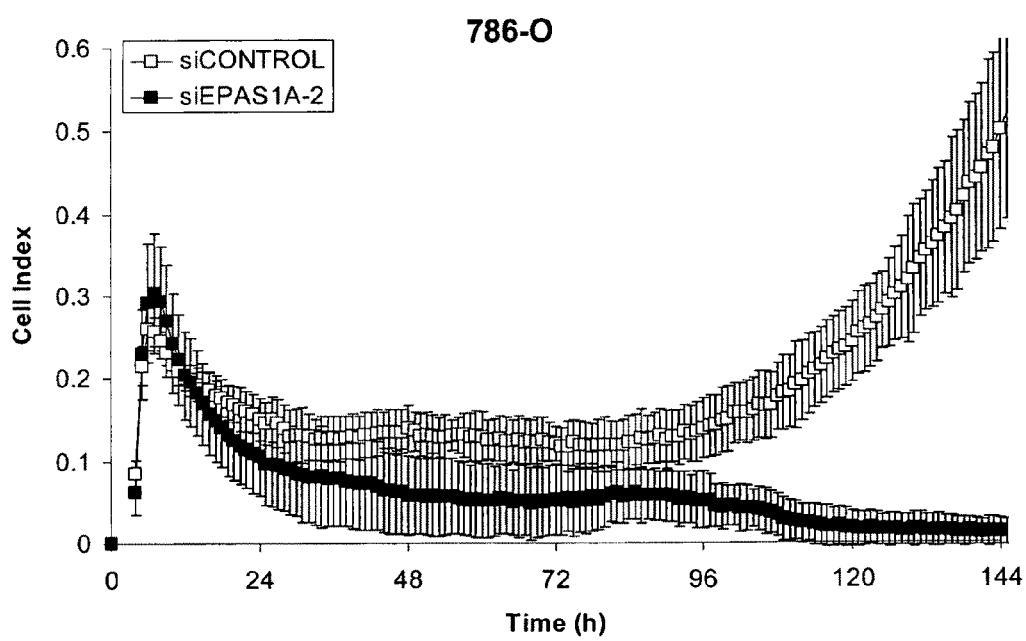

To examine the effect of siEPAS1A−2 on cellular proliferation rate, each of these three human RCC cell lines were transfected with siEPAS1A−2 or a non-targeting control siRNA (siCONTROL), each at 10 nM (A498 and Caki-1) or 20 nM (786-O) for 4 h, and their subsequent proliferation rates were measured using a real-time cell electronic sensing (RT-CES) assay system. Cell density was monitored regularly (every 60 min) for several days after transfection and quantified as a "cell index." Plots of cell index as a function of time post-transfection for the three different cells lines are shown in FIGS. 6A-6C (error bars represent the standard deviation of four replicate wells). As expected based upon VHL status, siEPAS1A−2 achieved a significant anti-proliferative effect in A498 and 786-O cells, but not in Caki-1 cells, indicating that cancer cells deficient in VHL are good candidates for treatment that reduces cellular HIF levels.

Those skilled in the art will recognize, or be able to ascertain using no more than routine experimentation, many equivalents to the specific embodiments of the invention described herein. Such equivalents are intended to be encompassed by the following claims.

All of the cited references and publications are hereby incorporated by reference in their entirety.

We claim:

1. A nucleic acid comprising:
   (i) a first strand of about 15 to about 30 nucleotides in length that comprises a sequence selected from SEQ ID NOs: 11, 13, 15, 17, 19, 21, 23, 25, 27, 29, 31, 33, 35, 37, 39 and 41, and
   (ii) a second strand of about 15 to about 30 nucleotides in length that comprises a sequence selected from SEQ ID NOs: 12, 14, 16, 18, 20, 22, 24, 26, 28, 30, 32, 34, 36, 38, 40, and 42,
   wherein at least 12 nucleotides of the first and second strands are complementary to each other and form a double-stranded nucleic acid under physiological conditions, and wherein the double-stranded nucleic acid can reduce the expression of endothelial PAS domain protein 1 (EPAS1) in a cell by an RNA interference mechanism.

2. The nucleic acid of claim 1, wherein the double-stranded portion is about 15 to about 30 nucleotides in length.

3. The nucleic acid of claim 1, wherein the nucleic acid is a hairpin RNA and the hairpin RNA comprises a loop region having about 4 to about 10 nucleotides in length.

4. The nucleic acid of claim 1, wherein the first strand is a DNA polynucleotide and the second strand is an RNA polynucleotide.

5. The nucleic acid of claim 1, wherein the first and/or second strand further comprises a 3' overhang region, a 5' overhang region, or both 3' and 5' overhang regions.

6. The nucleic acid of claim 5, wherein the overhang region contains about 1 to about 10 nucleotides in length.

7. The nucleic acid of claim 1, further comprising one or more modified backbone or base moieties selected from the group consisting of alkylphosphonates, phosphorothioates, phosphorodithioates, alkylphosphonothioates, phosphoramidates, phosphate esters, carbamates, acetamidate, carboxylmethyl esters, carbonates, and phosphate trimesters.

8. The nucleic acid of claim 7, wherein the modified backbone or base moieties comprise at least one 2'O-alkylated ribonucleotide.

9. The nucleic acid of claim 1, wherein the nucleic acid inhibits EPAS 1 expression in cells by 50% or greater, when contacted with the cells under physiological conditions at a concentration of 10 nanomolar.

10. The nucleic acid of claim 1, wherein the first strand comprises SEQ ID NO: 29, and the second strand comprises SEQ ID NO: 30.

11. The nucleic acid of claim 1, wherein the first strand consists of SEQ ID NO: 29, and the second strand consists of SEQ ID NO: 30.

12. An isolated nucleic acid comprising a sequence that hybridizes to a region of an EPAS1 transcript corresponding to nucleotides 655-718 of SEQ ID NO: 1 under physiological conditions and decreases the expression of EPAS 1 in a cell, comprising a first strand of about 15 to about 50 nucleotides in length that comprises a sequence selected from SEQ ID NOs: 11, 13, 15, 17, 19, 21, 23, 25, 27, 29, 31, 33, 35, 37, 39 and 41, and a second strand of about 15 to about 30 nucleotides in length that comprises a sequence selected from SEQ ID NOs: 14, 16, 18, 20, 22, 24, 26, 28, 30, 32, 34, 36, 38, 40, and 42.

13. The isolated nucleic acid of claim 12, wherein the nucleic acid is single-stranded.

14. The isolated nucleic acid of claim 12, wherein the nucleic acid is double-stranded.

15. The isolated nucleic acid of claim 12, wherein the nucleic acid is a DNA. molecule, comprising one or more modified backbone or base moieties.

16. The isolated nucleic acid of claim 12, wherein the nucleic acid is an RNA molecule, comprising one or more modified backbone or base moieties.

17. The isolated nucleic acid of claim 12, wherein the nucleic acid comprises a DNA strand and an RNA strand and one or more modified backbone or base moieties.

18. The isolated nucleic acid of claim 12, wherein the nucleic acid is an RNAi construct.

19. The isolated nucleic acid of claim 18, wherein the RNAi construct is a dsRNA comprising one more modified backbone or base moieties.

20. The isolated nucleic acid of claim 18, wherein the RNAi construct is a hairpin RNA, comprising one or more modified backbone or base moieties.

21. The isolated nucleic acid of claim 18, wherein the duplex portion of the RNAi construct is from about 15 to about 30 nucleotides in length.

22. The isolated nucleic acid of claim 12, further comprising at least one internucleotide linkage selected from the group consisting of alkylphosphonates, phosphorothioates, phosphorodithioates, alkylphosphonothioates, phosphoramidates, phosphate esters, carbamates, acetamidate, carboxylmethyl esters, carbonates, and phosphate trimesters.

23. The isolated nucleic acid of claim 12, further comprising at least one 2'-O -alkylated ribonucleotide.

24. The isolated nucleic acid of claim 12, wherein the nucleic acid is an enzymatic nucleic acid.

25. The isolated nucleic acid of claim 24, wherein the enzymatic. nucleic acid is a ribozyme.

26. The isolated nucleic acid of claim 24, wherein the enzymatic nucleic acid is a DNA enzyme.

27. The isolated nucleic acid of claim 12, wherein the nucleic acid inhibits EPAS 1 expression in cells by 50% or greater, when contacted with the cells under physiological conditions at a concentration of 10 nanomalar.

28. A pharmaceutical composition comprising the nucleic acid according to claim 1 or claim 12, and a pharmaceutically acceptable carrier.

29. The pharmaceutical composition of claim 28, wherein the pharmaceutically-acceptable carrier includes a cationic polymer.

30. The pharmaceutical composition of claim 28, wherein the pharmaceutically acceptable carrier includes a cyclodextrin polymer.

31. The pharmaceutical composition of claim 30, wherein the cyclodextrin structure is im-CDP.

32. The pharmaceutical composition of claim 30, wherein the cyclodextrin polymer is PEGylated.

33. The pharmaceutical composition of claim 30, wherein the carrier comprises adamantine.

34. The pharmaceutical composition of claim 30, wherein the carrier comprises a ligand that targets a particular tissue or cell type.

35. The pharmaceutical composition of claim 34, wherein the ligand is transferrin.

36. The pharmaceutical composition of claim 28, wherein the pharmaceutical composition comprises nanoparticles from about 10 to about 100 nm in diameter.

37. The pharmaceutical composition of claim 28, wherein the pharmaceutically acceptable carrier comprises an imidazole modified cyclodextrin-containing cationic polymer, and a targeting moiety comprising adamantane-PEG-ligand, wherein the polymer and targeting moiety form nanoparticles that encapsulate the nucleic and wherein the nanoparticles have a diameter of about 50 to about 120 nm.

38. The pharmaceutical composition of claim 37, wherein the targeting ligand is galactose.

39. The pharmaceutical composition of claim 37, wherein the targeting ligand is transferrin.

* * * * *

UNITED STATES PATENT AND TRADEMARK OFFICE
CERTIFICATE OF CORRECTION

| | |
|---|---|
| PATENT NO. | : 8,114,983 B2 |
| APPLICATION NO. | : 12/384475 |
| DATED | : February 14, 2012 |
| INVENTOR(S) | : Mark E. Davis et al. |

It is certified that error appears in the above-identified patent and that said Letters Patent is hereby corrected as shown below:

Column 85
Line 23 Claim 12, insert --12,-- before 14.

Signed and Sealed this
Seventeenth Day of April, 2012

David J. Kappos
*Director of the United States Patent and Trademark Office*

SEQUENCE LISTING

```
<160> NUMBER OF SEQ ID NOS: 84

<210> SEQ ID NO 1
<211> LENGTH: 5186
<212> TYPE: DNA
<213> ORGANISM: Homo sapiens

<400> SEQUENCE: 1
gccacacggg tccggtgccc gctgcgcttc cgccccagcg ctcctgaggc ggccgtacaa    60
```

-continued

```
tcctcggcag tgtcctgaga ctgtatggtc agctcagccc ggcctccgac tccttccgac    120
tcccagcatt cgagccactt ttttttttct ttgaaaactc agaaaagtga ctccttttcc    180
agggaaaaag gaacttgggt tcccttctct ccgtcctctt ttcgggtctg acagcctcca    240
cccactcctt ccccggaccc cgcctccgcg cgcaggttcc tcccagtcac ctttctccac    300
ccccgccccc gcacctagcc cgccgcgcgc caccttccac ctgactgcgc ggggcgctcg    360
ggacctgcgc gcacctcgga ccttcaccac ccgcccgggc cgcggggagc ggacgagggc    420
cacagccccc cacccgccag ggagcccagg tgctcggcgt ctgaacgtct caaagggcca    480
cagcgacaat gacagctgac aaggagaaga aaaggagtag ctcggagagg aggaaggaga    540
agtcccggga tgctgcgcgg tgccggcgga gcaaggagac ggaggtgttc tatgagctgg    600
cccatgagct gcctctgccc cacagtgtga gctcccatct ggacaaggcc tccatcatgc    660
gactggcaat cagcttcctg cgaacacaca agctcctctc ctcagtttgc tctgaaaacg    720
agtccgaagc cgaagctgac cagcagatgg acaacttgta cctgaaagcc ttggagggtt    780
tcattgccgt ggtgacccaa gatggcgaca tgatcttttct gtcagaaaac atcagcaagt    840
tcatgggact tacacaggtg gagctaacag gacatagtat ctttgacttc actcatccct    900
gcgaccatga ggagattcgt gagaacctga gtctcaaaaa tggctctggt tttgggaaaa    960
aaagcaaaga catgtccaca gagcgggact tcttcatgag gatgaagtgc acggtcacca   1020
acagaggccg tactgtcaac ctcaagtcag ccacctggaa ggtcttgcac tgcacgggcc   1080
aggtgaaagt ctacaacaac tgccctcctc acaatagtct gtgtggctac aaggagcccc   1140
tgctgtcctg cctcatcatc atgtgtgaac caatccagca cccatcccac atggacatcc   1200
ccctggatag caagaccttc ctgagccgcc acagcatgga catgaagttc acctactgtg   1260
atgacagaat cacagaactg attggttacc accctgagga gctgcttggc cgctcagcct   1320
atgaattcta ccatgcgcta gactccgaga acatgaccaa gagtcaccag aacttgtgca   1380
ccaagggtca ggtagtaagt ggccagtacc ggatgctcgc aaagcatggg ggctacgtgt   1440
ggctggagac ccaggggacg gtcatctaca cccctcgcaa cctgcagccc cagtgcatca   1500
tgtgtgtcaa ctacgtcctg agtgagattg agaagaatga cgtggtgttc tccatggacc   1560
agactgaatc cctgttcaag ccccacctga tggccatgaa cagcatcttt gatagcagtg   1620 gcaaggggc tgtgtctgag aagagtaact tccctattcac caagctaaag gaggagcccg   1680
aggagctggc ccagctggct cccaccccag gagacgccat catctctctg gatttcggga   1740
atcagaactt cgaggagtcc tcagcctatg caaggccatc cctgccccg agccagccat   1800 gggccacgga gttgaggagc cacagcaccc agagcgaggc tgggagcctg cctgccttca   1860
ccgtgcccca ggcagctgcc ccgggcagca ccaccccag tgccaccagc agcagcagca   1920
gctgctccac gcccaatagc cctgaagact attacacatc tttggataac gacctgaaga   1980
ttgaagtgat tgagaagctc ttcgccatgg acacagaggc caaggaccaa tgcagtaccc   2040
agacggattt caatgagctg gacttggaga cactggcacc ctatatcccc atggacgggg   2100
aagacttcca gctaagcccc atctgccccg aggagcggct cttggcggag aacccacagt   2160 ccaccccccca gcactgcttc agtgccatga caaacatctt ccagccactg gcccctgtag   2220
ccccgcacag tccttcctcc ctggacaagt ttcagcagca gctggagagc aagaagacag   2280
agcccgagca ccggcccatg tcctccatct tctttgatgc cggaagcaaa gcatccctgc   2340
caccgtgctg tggccaggcc agcacccctc tctcttccat ggggggcaga tccaataccc   2400
agtggccccc agatccacca ttacattttg ggcccacaaa gtgggccgtc ggggatcagc   2460
```

```
gcacagagtt cttgggagca gcgccgttgg ggccccctgt ctctccaccc catgtctcca    2520
ccttcaagac aaggtctgca aagggttttg gggctcgagg cccagacgtg ctgagtccgg    2580
ccatggtagc cctctccaac aagctgaagc tgaagcgaca gctggagtat aagagcaag     2640 ccttccagga cctgagcggg ggggacccac ctggtggcag cacctcacat tgatgtgga    2700 aacggatgaa gaacctcagg ggtgggagct gcccttttgat gccggacaag ccactgagcg   2760
caaatgtacc caatgataag ttcacccaaa accccatgag gggcctgggc catcccctga    2820
gacatctgcc gctgccacag cctccatctg ccatcagtcc cggggagaac agcaagagca    2880
ggttcccccc acagtgctac gccacccagt accaggacta cagcctgtcg tcagcccaca    2940
aggtgtcagg catggcaagc cggctgctcg ggccctcatt tgagtcctac ctgctgcccg    3000
aactgaccag atatgactgt gaggtgaacg tgcccgtgct gggaagctcc acgtcctgc     3060 aaggagggga cctcctcaga gccctggacc aggccacctg agccaggcct tctacctggg    3120
cagcacctct gccgacgccg tcccaccagc ttcactctct ccgtctgttt ttgcaactag    3180
gtatttctaa cgccagcaca ctatttacaa gatggactta cctggcagac ttgcccaggt    3240
caccaagcag tggcctttt ctgagatgct cactttatta tccctatttt taaagtacac     3300 aattgttta cctgttctga aatgttctta aattttgtag gattttttc ctccccacct      3360 tcaatgactt ctaatttata ttatccatag gtttctctcc ctccttctcc ttctcacaca    3420
caactgtcca tactaacaag tttggtgcat gtctgttctt ctgtagggag aagctttagc    3480
ttcattttac taaaaagatt cctcgttatt gttgttgcca aagagaaaca aaaatgattt    3540
tgctttccaa gcttggtttg tggcgtctcc ctcgcagagc ccttctcgtt tcttttttaa    3600
actaatcacc atattgtaaa tttcagggtt ttttttttt tgtttaagct gactctttgc     3660
tctaattttg gaaaaaaga aatgtgaagg gtcaactcca acgtatgtgg ttatctgtga    3720
aagttgcaca gcgtggcttt tcctaaactg gtgttttttcc cccgcatttg gtggattttt    3780
tattattatt caaaaacata actgagtttt ttaaaagagg agaaaattta tatctgggtt    3840
aagtgtttat catatatatg ggtactttgt aatatctaaa aacttagaaa cggaaatgga    3900
atcctgctca caaaatcact ttaagatctt ttcgaagctg ttaattttc ttagtgttgt     3960 ggacactgca gacttgtcca gtgctcccac ggcctgtacg gacactgtgg aaggcctccc   4020
tctgtcggct ttttgccatc tgtgatatgc cataggtgtg acaatccgag cagtggagtc    4080
attcagcggg agcactgcgc gctatcccct cacattctct atgtactatg tatgtatgta    4140 ttattatt tgctgccaag agggtctgat ggcacgttgt ggggtcgggg ggtgggggcgg    4200 ggaagtgctc taacttttct taaggttttg ttgctagccc ttcaagtgca ctgagctatg    4260
tgactcggat ggtcttttcac acggcacatt tggacatttc cagaactacc atgagatggt    4320
ttagacggga attcatgcaa atgaggggtc aaaaatggta tagtgacccc gtccacgtcc    4380
tccaagctca cgaccttgga gccccgtgga gctggactga ggaggaggct gcacagcggg    4440
agagcagctg gtccagacca gccctgcagc ccccactcag ccggcagcca gatggccccg    4500
caaggcctcc agggatggcc cctagccaca ggccctggct gaggtctctg ggtcggtcag    4560
tgacatgtag gtaggaagca ctgaaaatag tgttcccaga gcactttgca actccctggg    4620
taagagggac gacacctctg gttttcaat accaattaca tggaactttt ctgtaatggg     4680
tacaatgaag aagtttctaa aaacacacac aaagcacatt gggccaacta tttagtaagc    4740
ccggatagac ttattgccaa aaacaaaaaa tagcttcaa aagaaattta agttctatga     4800
gaaattcctt agtcatggtg ttgcgtaaat catatttag ctgcacggca ttaccccaca     4860
```

-continued

```
cagggtggca gaacttgaag ggttactgac gtgtaaatgc tggtatttga tttcctgtgt      4920
gtgttgccct ggcattaagg gcattttacc cttgcagttt tactaaaaca ctgaaaaata      4980
ttccaagctt catattaacc ctacctgtca acgtaacgat ttcatgaacg ttattatatt      5040
gtcgaattcc tactgacaac attataactg tatgggagct taactttata aggaaatgta      5100
ttttgacact ggtatcttat taaagtattc tgatcctaaa aaaaaaaaaa aaaaaaaaa       5160 aaaaaaaaaa aaaaaaaaaa aaaaa                                            5186

<210> SEQ ID NO 2
<211> LENGTH: 11
<212> TYPE: RNA
<213> ORGANISM: Homo sapiens

<400> SEQUENCE: 2
acacacaagc u                                                             11

<210> SEQ ID NO 3
<211> LENGTH: 11
<212> TYPE: RNA
<213> ORGANISM: Homo sapiens

<400> SEQUENCE: 3
gccacccagu a                                                             11

<210> SEQ ID NO 4
<211> LENGTH: 11
<212> TYPE: RNA
<213> ORGANISM: Homo sapiens

<400> SEQUENCE: 4
ugucaacgua a                                                             11

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ugcgaacaca caagcuccuc u                                                  21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aggagcuugu guuucgcag g                                                   21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcuacgccac ccaguaccag g                                                  21
```

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugguacuggg uggcguagca c                                                 21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cuaccuguca acguaacgau u                                                 21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucguuacguu gacagguagg g                                                 21

<210> SEQ ID NO 11
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
ugcgaacaca caagcuccuc ucctc                                             25

<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaggagagga gcuugugugu ucgcagg                                           27

<210> SEQ ID NO 13
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gcuuccugcg aacacacaag cuccucu        27

<210> SEQ ID NO 14
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
ggagcuugug uguucgcagg aagc        24

<210> SEQ ID NO 15
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
gcuacgccac ccaguaccag gacta        25

<210> SEQ ID NO 16
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uaguccuggu acuggguggc guagcac        27

<210> SEQ ID NO 17
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cacagugcua cgccacccag uaccagg        27

<210> SEQ ID NO 18
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
ugguacuggg uggcguagca cugtg        25

<210> SEQ ID NO 19
<211> LENGTH: 25
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
cuaccuguca acguaacgau uucat                                          25

<210> SEQ ID NO 20
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
augaaaucgu uacguugaca gguaggg                                        27

<210> SEQ ID NO 21
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuaacccuac cugucaacgu aacgauu                                        27

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucguuacguu gacagguagg guuaa                                          25

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cuuccugcga acacacaagc u                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cuuguguguu cgcaggaagc u                                              21

<210> SEQ ID NO 25
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuccugcgaa cacacaagcu c                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gcuugugugu ucgcaggaag c                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uccugcgaac acacaagcuc c                                              21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
agcuugugug uucgcaggaa g                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccugcgaaca cacaagcucc u                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gagcuugugu guucgcagga a                                              21

<210> SEQ ID NO 31
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 31
cugcgaacac acaagcuccu c                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagcuugug uguucgcagg a                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gcgaacacac aagcuccucu c                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gaggagcuug uguguucgca g                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cgaacacaca agcuccucuc c                                              21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
agaggagcuu guguguucgc a                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 37
gaacacacaa gcuccucucc u                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gagaggagcu uguguguucg c                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aacacacaag cuccucuccu c                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggagaggagc uuguguguuc g                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
acacacaagc uccucuccuc a                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aggagaggag cuuguguguu c                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 43
acagugcuac gccacccagu a                                         21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cuggguggcg uagcacugug g                                         21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cagugcuacg ccacccagua c                                         21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
acuggguggc guagcacugu g                                         21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
agugcuacgc cacccaguac c                                         21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uacugggugg cguagcacug u                                         21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
```
gugcuacgcc acccaguacc a        21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
guacugggug gcguagcacu g        21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ugcuacgcca cccaguacca g        21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gguacugggu ggcguagcac u        21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cuacgccacc caguaccagg a        21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cugguacugg guggcguagc a        21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uacgccaccc aguaccagga c        21

-continued

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ccugguacug gguggcguag c                                             21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
acgccaccca guaccaggac u                                             21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uccugguacu ggguggcgua g                                             21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cgccacccag uaccaggacu a                                             21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
guccugguac uggguggcgu a                                             21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gccacccagu accaggacua c                                             21

<210> SEQ ID NO 62

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aguccuggua cuggguggcg u                                             21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uaacccuacc ugucaacgua a                                             21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
acguugacag guaggguuaa u                                             21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aacccuaccu gucaacguaa c                                             21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uacguugaca gguaggguua a                                             21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acccuaccug ucaacguaac g                                             21

<210> SEQ ID NO 68
<211> LENGTH: 21
<212> TYPE: RNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 68
uuacguugac agguagggun a                                              21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cccuaccugu caacguaacg a                                              21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
guuacguuga cagguagggu u                                              21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ccuaccuguc aacguaacga u                                              21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cguuacguug acagguaggg u                                              21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uaccugucaa cguaacgauu u                                              21

<210> SEQ ID NO 74
<211> LENGTH: 21
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 74
aucguuacgu ugacagguag g                                              21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
accugucaac guaacgauuu c                                              21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aaucguuacg uugacaggua g                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ccugucaacg uaacgauuuc a                                              21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aaaucguuac guugacaggu a                                              21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cugucaacgu aacgauuuca u                                              21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 80
gaaaucguua cguugacagg u                                              21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ugucaacgua acgauuucau g                                              21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ugaaaucguu acguugacag g                                              21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uagcgacuaa acacaucaau u                                              21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uugauguguu uagucgcuau u                                              21
```